United States Patent
Mellors et al.

(10) Patent No.: US 9,502,225 B2
(45) Date of Patent: Nov. 22, 2016

(54) INTEGRATED SAMPLE PROCESSING FOR ELECTROSPRAY IONIZATION DEVICES

(71) Applicant: The University of North Carolina at Chapel Hill, Chapel Hill, NC (US)

(72) Inventors: John Scott Mellors, Chapel Hill, NC (US);
(Continued)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/402,278

(22) PCT Filed: Jun. 5, 2013

(86) PCT No.: PCT/US2013/044266
§ 371 (c)(1),
(2) Date: Nov. 19, 2014

(87) PCT Pub. No.: WO2013/191908
PCT Pub. Date: Dec. 27, 2013

(65) Prior Publication Data
US 2015/0340219 A1     Nov. 26, 2015

Related U.S. Application Data

(60) Provisional application No. 61/662,152, filed on Jun. 20, 2012.

(51) Int. Cl.
*H01J 49/04* (2006.01)
*H01J 49/26* (2006.01)
(Continued)

(52) U.S. Cl.
CPC ....... *H01J 49/0431* (2013.01); *G01N 27/4473* (2013.01); *G01N 27/44791* (2013.01);
(Continued)

(58) Field of Classification Search
None
See application file for complete search history.

(56) References Cited

U.S. PATENT DOCUMENTS

| | | |
|---|---|---|
| 6,110,343 A | 8/2000 | Ramsey et al. |
| 6,231,737 B1 | 5/2001 | Ramsey et al. |

(Continued)

FOREIGN PATENT DOCUMENTS

| | | |
|---|---|---|
| WO | WO2009/011488 | 1/2009 |
| WO | WO 2009/109037 A1 | 9/2009 |

(Continued)

OTHER PUBLICATIONS

Sikanen et al., "Fully microfabricated and integrated Su-8-Based Capillary Electrophoresis-Electrospray Ionization Microchips for Mass Spectrometry", Anal. Chem. 2007.*
(Continued)

*Primary Examiner* — Michael Logie
(74) *Attorney, Agent, or Firm* — Myers Bigel & Sibley, P.A.

(57) ABSTRACT

Methods, systems and devices that generate differential axial transport in a fluidic device having at least one fluidic sample separation flow channel and at least one ESI emitter in communication with the at least one sample separation flow channel. In response to the generated differential axial transport, the at least one target analyte contained in a sample reservoir in communication with the sample separation channel is selectively transported to the at least one ESI emitter while inhibiting transport of contaminant materials contained in the sample reservoir toward the at least one ESI emitter thereby preferentially directing analyte molecules out of the at least one ESI emitter. The methods, systems and devices are particularly suitable for use with a mass spectrometer.

22 Claims, 18 Drawing Sheets

(72) Inventors: John Michael Ramsey, Chapel Hill, NC (US); Nicholas George Batz, Carrboro, NC (US)

(51) Int. Cl.
*H01J 49/16* (2006.01)
*G01N 27/447* (2006.01)

(52) U.S. Cl.
CPC .............. *H01J 49/165* (2013.01); *H01J 49/26* (2013.01); *G01N 27/44743* (2013.01)

(56) References Cited

U.S. PATENT DOCUMENTS

| | | | |
|---|---|---|---|
| 6,685,813 B2 * | 2/2004 | Williams .............. | B01L 3/5027 204/549 |
| 7,449,686 B2 | 11/2008 | Wang et al. | |
| 8,030,092 B2 | 10/2011 | Guzman | |
| 8,097,472 B2 | 1/2012 | Schneider et al. | |
| 8,277,659 B2 * | 10/2012 | Sun .................. | G01N 27/44743 204/452 |
| 2003/0015425 A1 * | 1/2003 | Bohm ..................... | B01D 57/02 204/453 |
| 2003/0047680 A1 * | 3/2003 | Figeys ................ | B01L 3/50273 250/288 |
| 2003/0070925 A1 * | 4/2003 | Voss ................. | G01N 27/44743 204/453 |
| 2004/0195099 A1 * | 10/2004 | Jacobson ............... | B01D 57/02 204/450 |
| 2005/0047969 A1 * | 3/2005 | Zhao ..................... | B01L 3/0268 422/503 |
| 2005/0133371 A1 * | 6/2005 | Timperman ..... | G01N 27/44752 204/450 |
| 2006/0285999 A1 * | 12/2006 | Timperman ...... | B01L 3/502746 422/400 |
| 2008/0223722 A1 * | 9/2008 | Guzman .......... | G01N 27/44743 204/453 |
| 2011/0042216 A1 * | 2/2011 | Maxwell ............ | G01N 27/4473 204/604 |
| 2011/0309244 A1 | 12/2011 | Whitehouse et al. | |
| 2012/0083046 A1 * | 4/2012 | Watson ............. | B01L 3/502715 436/177 |

FOREIGN PATENT DOCUMENTS

WO  WO 2012/040098 A2  3/2012
WO  WO 2012/125318 A2  9/2012

OTHER PUBLICATIONS

Mellors et al. "Fully Integrated Glass Microfluidic Device for Performing High-Efficiency Capillary Electrophoresis and Electrospray Ionization Mass Spectrometry", Anal. Chem. 2008.*
Mellors et al. "Integrated Microfluidic Device for Automated Single Cell Analysis Using Electrophoretic Separation and Electrospray ionization Mass Spectrometry", Anal. Chem. 2010.*
Ullsten et al. "A polyamine coating for enhanced capillary electrophoresis-electrospray ionization-mass spectrometry of proteins and peptides", Electrophoresis 2004.*
Smith et al. "Capillary Zone Electrophoresis—Mass Spectrometry using an electrospray Ionization Interface", Analytical Chemistry 1988.*
International Search Report and Written Opinion Corresponding to International Application No. PCT/US2013/044266; Date of Mailing: Oct. 24, 2013; 9 Pages.
Belder et al. "Cross-linked poly(vinyl alcohol) as permanent hydrophilic column coating for capillary electrophoresis" *Electrophoresis*, 2001. 22(17): p. 3813-3818.
Chambers et al. "Monolithic Integration of Two-Dimensional Liquid Chromatography-Capillary electrophoresis and Electrospray Ionization on a Microfluidic Device", *Analytical Chemistry*, Feb. 1, 2011, 83:842-849.
Chen et al. "Surface Modification of Silicate Glass Using 3-Mercaptopropyl)trimethoxysilane for Thiol-Ene Polymerization", *Langmuir*, 2011. 27(22): p. 13754-13761.
Culbertson et al. "Electroosmotically Induced Hydraulic Pumping on Microchips: Differential Ion Transport", *Anal Chem.*, 2000, 72:2285-2291.
Dutta et al. "A microfluidic device for performing pressure-driven separations", *Lab on a Chip*, 2011, 11:3081-3088.
Fenn et al. "Electrospray ionization for mass-spectrometry of large biomolecules", *Science*, 1989, 246:64-71.
Gottschlich et al. "Two-Dimensional Electrochromatography/Capillary Electrophoresis on a Microchip", *Anal Chem.*, 2001, 73:2669-2674.
Haselberg et al. "Capillary electrophoresis of intact basic proteins using noncovalently triple-layer coated capillaries", *Journal of Separation Science*, 2009. 32(14): p. 2408-2415.
Hensel et al. "Electrospray sample preparation for improved quantitation in matrix-assisted laser desorption/ionization time-of-flight mass spectrometry", *Rapid Communications in Mass Spectrometry*, 1997, 11:1785-1793.
Jacobson et al. "Microchip Structures for Submillisecond Electrophoresis", *Anal Chem.*, 1998, 70:3476-3480.
Lindner et al., "Effect of Buffer Composition on the Migration Order and Separation of Histone H1 Subtypes" *Electrophoresis*, 1995. 16(4): p. 604-610.
McClain et al. "Microfluidic Devices for the High-Throughput Chemical Analysis of Cells", Anal Chem., 2003, 75:5646-5655.
Mellors et al. "Fully integrated glass microfluidic device for performing high-efficiency capillary electrophoresis and electrospray ionization mass spectrometry", *Anal Chem*, 2008, 80(18), 6881-6887.
Morozov, Electrospray Deposition of Biomolecules, *Advance Biochem Engin, Nano/Micro Biotechnology*, 2010, vol. 119, pp. 115-162.
Ramautar et al., "Capillary electrophoresis-time of flight-mass spectrometry using noncovalently bilayer-coated capillaries for the analysis of amino acids in human urine" *Electrophoresis*, 2008. 29(12): p. 2714-2722.
Ramsey et al. "Generating Electrospray from Microchip Devices Using Electroosmotic Pumping", *Anal Chem*, 1997, 69:1174-1178.
Ramsey et al. "High-Efficiency, Two-dimensional Separations of Protein Digests on Microfluidic Devices", *Anal Chem.*, 2003, 75:3758-3764.
Razunguzwa et al., "ESI-MS compatible permanent coating of glass surfaces using poly(ethylene glycol)-terminated alkoxysilanes for capillary zone electrophoretic protein separations" *Analytical Chemistry*, 2006. 78(13): p. 4326-4333.
Thorsteinsdottir et al. "Performance of Amino-Silylated Fused-Silica Capillaries for the Separation of Enkephalin-Related Peptides by Capillary Zone Electrophoresis and Micellar Electrokinetic Chromatography", *Electrophoresis*, 1995. 16(4): p. 557-563.
Ullsten et al., "A polyamine coating for enhanced capillary electrophoresis-electrospray ionization-mass spectrometry of proteins and peptides" *Electrophoresis*, 2004. 25(13): p. 2090-2099.
Wang et al., "Covalent modified hydrophilic polymer brushes onto poly(dimethylsiloxane) microchannel surface for electrophoresis separation of amino acids" *Journal of Chromatography A*, 2008. 1192(1): p. 173-179.
Xu et al., "Preparation of a sulfonated fused-silica capillary and its application in capillary electrophoresis and electrochromatography" *Journal of Chromatography A*, 2004. 1033(1): p. 161-166.
Xue et al. "Multichannel Microchip Electrospray Mass Spectrometry", *Anal Chem*, Feb. 1, 1997, 69:426-430.
Extended European Search Report for related EP Application No. 13806595.8, Mar. 30, 2016, 15 pages.

* cited by examiner

MASS SPECTRA OBTAINED BY INFUSING mAb SAMPLES THROUGH THE SYRINGE PUMP INFUSION-ESI SYSTEM. EACH SPECTRUM IS A SUMMATION OF 5 MINUTES OF DATA.

MASS SPECTRA OBTAINED BY INFUSING mAb SAMPLES THROUGH THE SYRINGE PUMP INFUSION-ESI SYSTEM. EACH SPECTRUM IS A SUMMATION OF 5 MINUTES OF DATA.

MASS SPECTRA OBTAINED BY INFUSING mAb SAMPLES THROUGH THE MICROFLUIDIC INFUSION-ESI DEVICE.
EACH SPECTRUM IS A SUMMATION OF 5 MINUTES OF DATA.

MASS SPECTRA OBTAINED BY INFUSING mAb SAMPLES THROUGH THE MICROFLUIDIC INFUSION-ESI DEVICE.
EACH SPECTRUM IS A SUMMATION OF 5 MINUTES OF DATA.

ns spectrometry. See, e.g., Cole, R. B. *Electrospray Ionization Mass Spectrometry: Fundamentals, Instrumentation & Applications;* John Wiley and Sons, Inc.: New York, 1997. Electrospray ionization was developed in the late 1980s and was popularized by the work of Fenn. See, e.g., Fenn J B, Mann M, Meng C K, Wong S F & Whitehouse C M (1989), Electrospray ionization for mass-spectrometry of large biomolecules. *Science* 246, 64-71. Simplistically, electrospray ionization involves the use of electric fields to disperse a sample solution into charged droplets. Through subsequent evaporation of the droplets, analyte ions contained in the droplet are either field emitted from the droplet surface or the ions are desolvated resulting in gas phase analyte ions. The source of the liquid exposed to the electric field and to be dispersed is ideally one of small areal extent as the size of the electrospray emitter directly influences the size of droplets produced. Smaller droplets desolvate more rapidly and have fewer molecules present per droplet leading to greater ionization efficiencies. These ions can be characterized by a mass analyzer to determine the mass-to-charge ratio. Further analyte structural information can be obtained by employing tandem mass spectrometry techniques.

INTEGRATED SAMPLE PROCESSING FOR ELECTROSPRAY IONIZATION DEVICES

RELATED APPLICATIONS

This application claims priority to and the benefit of U.S. Provisional Application Ser. No. 61/662,152, filed Jun. 20, 2012, the contents of which are hereby incorporated by reference as if recited in full herein.

FIELD OF THE INVENTION

This invention is related to electrospray ionization devices that are particularly suitable for infusion-based devices that interface with mass spectrometers.

BACKGROUND OF THE INVENTION

Electrospray ionization ("ESI") is an important technique for the analysis of biological materials contained in solution by mass spectrometry. See, e.g., Cole, R. B. *Electrospray Ionization Mass Spectrometry: Fundamentals, Instrumentation & Applications;* John Wiley and Sons, Inc.: New York, 1997. Electrospray ionization was developed in the late 1980s and was popularized by the work of Fenn. See, e.g., Fenn J B, Mann M, Meng C K, Wong S F & Whitehouse C M (1989), Electrospray ionization for mass-spectrometry of large biomolecules. *Science* 246, 64-71. Simplistically, electrospray ionization involves the use of electric fields to disperse a sample solution into charged droplets. Through subsequent evaporation of the droplets, analyte ions contained in the droplet are either field emitted from the droplet surface or the ions are desolvated resulting in gas phase analyte ions. The source of the liquid exposed to the electric field and to be dispersed is ideally one of small areal extent as the size of the electrospray emitter directly influences the size of droplets produced. Smaller droplets desolvate more rapidly and have fewer molecules present per droplet leading to greater ionization efficiencies. These ions can be characterized by a mass analyzer to determine the mass-to-charge ratio. Further analyte structural information can be obtained by employing tandem mass spectrometry techniques.

The chemical informing power of electrospray ionization—mass spectrometry can be enhanced when the electrospray emitter is coupled to liquid-phase chemical separations such as liquid chromatography, capillary electrophoresis, or ion exchange chromatography, to name a few. These chemical separation techniques endeavor to deliver isolated compounds to the electrospray emitter to reduce ionization suppression and mass spectral complexity.

When performing electrospray ionization-mass spectrometry (ESI-MS) it is often necessary to first remove unwanted components of the sample matrix. These unwanted components can cause a number of problems for ESI-MS including: ionization suppression, complexation with analyte ions, and fouling of the mass spectrometer inlet. For large molecules, like intact proteins that generate complex mass spectra, common sample matrix components like surfactants and buffer salts can render the mass spectrum unintelligible. Furthermore, it is often difficult and time consuming to completely remove these unwanted components by conventional methods.

SUMMARY OF EMBODIMENTS OF THE INVENTION

Embodiments of the invention provide systems, methods and devices configured to generate online sample processing using differential axial transport between analytes of interest and contaminate materials.

Embodiments of the invention are directed to methods for online sample processing for electrospray ionization (which may be particularly useful for mass spectrometry). The methods include: (a) generating differential axial transport in a fluidic device having at least one fluidic sample separation flow channel and at least one ESI emitter in communication with the at least one sample separation flow channel; and (b) in response to the generated differential axial transport, selectively transporting at least one target analyte contained in a sample reservoir in communication with the sample separation flow channel to the ESI emitter while inhibiting transport of contaminant materials contained in the sample reservoir to the ESI emitter. The analyte molecules thus being preferentially directed out of the ESI emitter.

The at least one target analyte can include a protein and the at least one non-analyte component can include a surfactant.

The fluidic device can have at least one background electrolyte (BGE) flow channel, a respective BGE channel merging into a respective separation channel at a junction proximate the at least one emitter. Generating the differential axial transport can include: (i) applying a first voltage proximate an ingress end portion of the separation channel; (ii) concurrently applying a second different voltage proximate an ingress end portion of the BGE channel; and (iii) generating axial EOF in the separation and BGE channels in response to the application of the voltages so that the EOF in the BGE channel has a greater mobility than that in the separation channel.

The fluidic device can have at least one sample reservoir that feeds the sample separation flow channel. The fluidic device can include at least one BGE reservoir and associated BGE channel in communication with the at least one sample separation flow channel. Generating the differential axial transport and the selective transport can be carried out by: (i) applying a first voltage to the sample reservoir; (ii) applying a second voltage to the BGE reservoir; and (iii) generating an EOF in the sample separation flow channel that is toward the sample reservoir and away from the ESI emitter; and (iv) generating an EOF in the BGE channel, with the EOF flow in the BGE channel being greater than the EOF flow in the separation channel.

In particular embodiments, the analyte can have an electrophoretic velocity that is above the EOF of the separation channel and the non-analyte component can have less mobility than the target analyte such that there is selective transport of the at least one target analyte from the sample reservoir against the EOF in the separation channel toward the at least one ESI emitter and the non-analyte remains in the sample reservoir.

The selective transport can be carried out by allowing high mobility cationic analyte molecules to migrate against the EOF in the separation channel from a sample reservoir toward the ESI emitter while low mobility cations, anions, and neutrals remain in the sample reservoir.

The selective transport can be carried out by causing high mobility anionic analyte molecules to migrate against the EOF in the separation channel toward the ESI emitter while low mobility anions, cations, and neutrals remain in a sample reservoir holding a supply of the sample, the sample reservoir being in fluid communication with the separation channel.

The EOF in the BGE channel can be greater than that in the separation channel and can define an EO pump that drives fluid with the at least one analyte out of the at least one emitter to spray toward a collection device for subsequent analysis and/or toward an inlet of a mass spectrometer.

The fluidic device can be a capillary device with the separation channel defined by a capillary tube.

The fluidic device can be a microfluidic chip.

The method can include spraying fluid with the analyte out the at least one emitter in a substantially stable stream or plume for periods of time sufficient for generating signal averaged mass spectra, ion mobility spectra, or for collection of the analyte onto a plate for MALDI analysis of the analyte.

The at least one target analyte can include intact monoclonal antibodies.

Other embodiments are directed to mass spectrometer analyzer systems with integrated online sample processing (e.g., cleaning). The systems include: (a) a mass spectrometer with an inlet orifice; (b) a fluidic device having at least one sample reservoir, at least one fluidic sample separation flow channel that is in fluid communication with a respective sample reservoir, at least one background electrolyte reservoir with an associated (BGE) flow channel, and at least one ESI emitter in communication with the at least one sample separation flow channel, wherein a respective BGE flow channel merges into a respective separation channel at a junction proximate the at least one emitter; and (c) at least one power source having a first voltage input in communication with the sample reservoir and a second voltage input in communication with the BGE reservoir, wherein, in operation, the first and second voltage inputs are both (e.g., substantially constantly) powered with one of the first and second voltages being greater than the other to generate axial electroosmotic flow (EOF) in the separation and BGE channels so that the EOF in the BGE channel has a greater mobility than that in the separation channel.

Optionally, the EOF mobility in the separation channel can be less than an electrophoresis of the at least one target analyte. The fluidic device can include a dirty sample in the sample reservoir. The at least one target analyte can migrate against the EOF in the separation channel to be emitted by the emitter while at least one unwanted non-analyte remains in the separation channel due to electrophoretic mobility bias to thereby provide integrated online sample cleaning.

The magnitude and direction of the EOF can be dictated by the channel surface chemistry.

The system can include a control circuit configured to control application of the voltages to generate the EOF.

Surfaces of the at least one separation channel can have a negative charge (cathodic EOF). In operation, the at least one separation channel can be configured to allow high mobility anions of the at least one target analyte to migrate against the EOF in the separation channel from the sample reservoir toward the ESI emitter while low mobility anions, cations, and neutrals remain in the sample reservoir.

Surfaces of the at least one separation channel can have a positive charge (anodic EOF). In operation, the at least one separation channel can be configured to allow high mobility cations of the analyte to migrate against the EOF in the separation channel toward the ESI emitter while low mobility cations, anions, and neutrals remain in the sample reservoir.

Surfaces of the at least one separation channel can have a negative charge. In operation, the at least one separation channel can be configured to allow the at least one target analyte to migrate with the EOF in the separation channel from the sample reservoir toward the ESI emitter.

Surfaces of the at least one separation channel can have a positive charge. In operation, the at least one separation channel can be configured to allow the analyte to migrate with the EOF in the separation channel toward the ESI emitter.

Other embodiments are directed to microfluidic devices for infusion-electrospray ionization-mass spectroscopy. The devices include: (a) a background electrolyte (BGE) reservoir; (b) a BGE channel in fluid communication with the BGE reservoir; (c) a sample reservoir; (d) a separation channel in fluid communication with the sample reservoir, the separation channel having a defined positive or negative charge and a modified electroosmotic flow surface coating that reduces EOF flow along an entire length thereof from the sample reservoir to a junction defined by an intersection of the BGE channel with the separation channel; and (e) at least one emitter in fluid communication with the separation channel and the BGE channel proximate to but downstream of the junction.

The BGE reservoir, BGE channel, sample reservoir, separation channel and at least one emitter can be held on a microchip.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DESCRIPTION OF EMBODIMENTS OF THE INVENTION

Figure 1A:
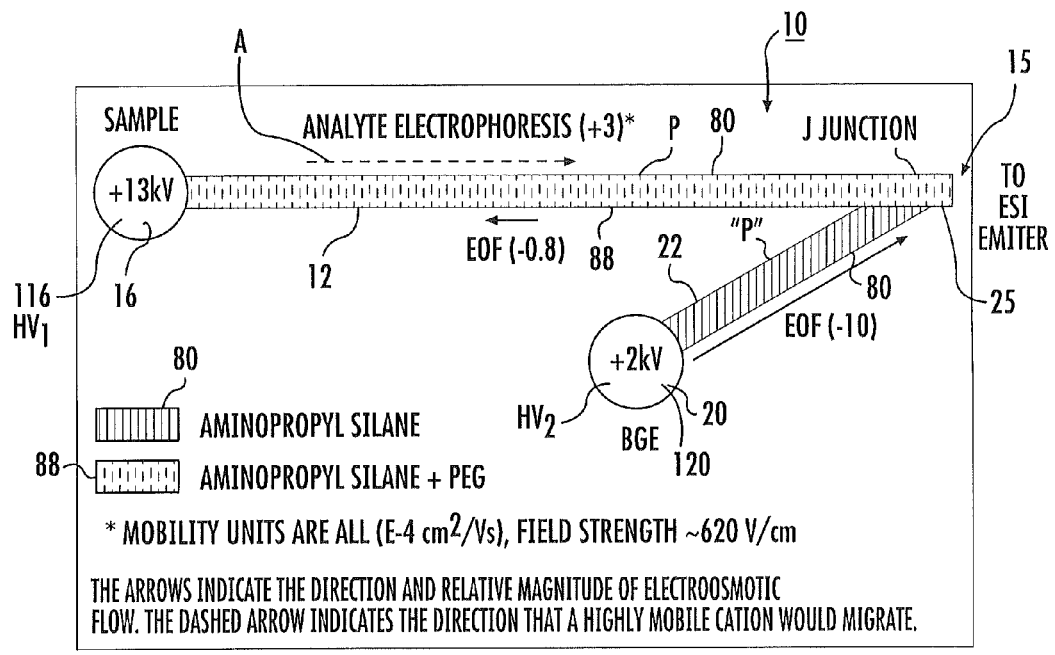
FIG. 1A is a schematic illustration of an exemplary fluidic device according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "about" means that the stated number can vary from that value by +/−20%.

The term "analyte" refers to a molecule or substance undergoing analysis, typically, at least for mass spectrometry analysis, having an ion or ions of interest in a m/z range of interest. The analyte can comprise biomolecules such as polymers, peptides, proteins and the like. Embodiments of the invention are particularly suitable for analyzing intact monoclonal antibodies.

The term "online sample processing" refers to separation of one or more non-analyte sample constituents (e.g., contaminant materials) from one or more target analytes in a respective sample during electrospray emission of fluid with the analyte(s) undergoing analysis. Unwanted non-analyte sample constituents (e.g., contaminant materials) can include impurities such as surfactants and/or buffers that might otherwise result in ESI-MS spectra that occludes or interferes with the generation of mass spectra, or other measurement information, of the analyte itself. The unwanted non-analyte(s) can have an ion or ions of interest in an m/z range of interest that may overlap that of one or more target analytes. Similarly, the term "dirty sample" refers to a sample that has a target analyte and other unwanted non-analytes as noted above. Thus, a dirty sample is a sample that has not been pre-cleaned, filtered or processed to remove unwanted components.

The term "differential axial transport" means the use of hydraulic transport configured so that net transport of the analyte(s) is toward one or more ESI emitters without the contaminants in the sample/sample reservoir. The differential axial transport can include any combination of EOF (magnitude and direction), electrophoretic mobility (magnitude and direction) used with or without pressure-driven flow.

The term "microchip" refers to a substantially planar, thin, and, in some embodiments, rigid device. The term "thin" refers to a thickness dimension that is less than about 10 mm, typically about 1 mm or less. The microchip typically has a width and length that is less than about 6 inches and a thickness that is less than about 5 mm, typically between about 2000 μm to about 250 μm.

The terms "integrated" and "integral" and derivatives thereof means that the component or process is incorporated into or carried out by a fluidic device.

The term "high voltage" refers to voltage in the kV range, typically between about 1-100 kV, more typically between about 1-20 kV. Lower voltages may be used for precessing and/or in certain embodiments, ESI processes can employ potentials of a few kVs.

The term "microfluidic" refers to fluid flow channels that have sub-millimeter or smaller size width and/or depth (e.g., the term includes nanometer size channels) and includes channels with width or depth in a size range of about tens to hundreds of microns.

All of the document references (patents, patent applications and articles) are hereby incorporated by reference as if recited in full herein.

In typical free zone capillary electrophoresis (CE) experiments, a sample plug is injected into a column, and an applied electric field causes sample components to separate by differences in their mobilities. The mobility of a molecule is the sum of its electrophoretic mobility and the electroosmotic mobility, and any pressure driven flow, if present, of the separation column.

When the electroosmotic mobility is greater than the electrophoretic mobility of each sample component (e.g., constituent), all components migrate in the same direction. However, when the electroosmotic mobility is low, species with a higher electrophoretic mobility of opposite sign (polarity or charge) will migrate against the electroosmotic flow (EOF). Generally stated, embodiments of the invention use the latter property for online sample processing to separate analyte molecules from sample matrix components, if the analyte molecules have sufficiently different electrophoretic mobilities than the other components. If the (CE) separation channel has a low electroosmotic mobility, analyte molecules with sufficiently high electrophoretic mobility can be constantly drawn out of a sample matrix by the application of an appropriate electric field. Sample components that do not have sufficient mobility will remain in the sample reservoir. With an appropriate ESI interface, analyte molecules migrating down the separation column or channel can be constantly sprayed or infused into a mass spectrometer, or into or onto other devices.

The total mobility (μ or "mobility") of a molecule can define its velocity (v) in an electric field (E):

$$v_1 = \mu_1 E \qquad \text{Equation (1)}$$

The total mobility of a molecule is the sum of its electrophoretic mobility ($\mu_{EP}$) and the electroosmotic mobility ($\mu_{EO}$) of a transport channel.

$$\mu_1 = \mu_{EP1} + \mu_{EO} \qquad \text{Equation (2)}$$

If pressure-driven flow is also present in the transport channel, then the pressure-driven flow can either diminish or enhance the bulk electroosmotic flow. Because pressure-driven flow is independent from the electric field, Equation (1) can be modified to include a pressure-driven velocity ($v_P$) component or term to modify the observed velocity in the presence of pressure-driven flow per Equation (3).

$$v_1 = \mu_1 E + v_P \qquad \text{Equation (3)}$$

To facilitate differential axial transport, the observed velocity of a target analyte ($v_1$) should be toward the ESI emitter or detector end of the transport (e.g., separation) channel, while the observed velocity or velocities of the contaminant(s) or impurities ($v_i$) can be in the opposite direction. If $v_1$ is positive, then $v_i$ is negative and vice versa. As long as the electrophoretic mobilities $\mu_1$ and $\mu_i$ are sufficiently different, conditions can be engineered to yield $v_1$ and $v_i$ values of opposite sign. Therefore, the electrophoretic mobility of the analyte is not always required to be (but can be) greater than that of the contaminants or impurities in a respective sample. In addition, the electrophoretic mobility of the analyte is not required to be opposite that of the contaminant or impurities. The analyte can migrate against the EOF as discussed herein in some embodiments. However, in some embodiments, the impurities can migrate against the EOF, and the analyte can migrate with the EOF.

Figure 1B:
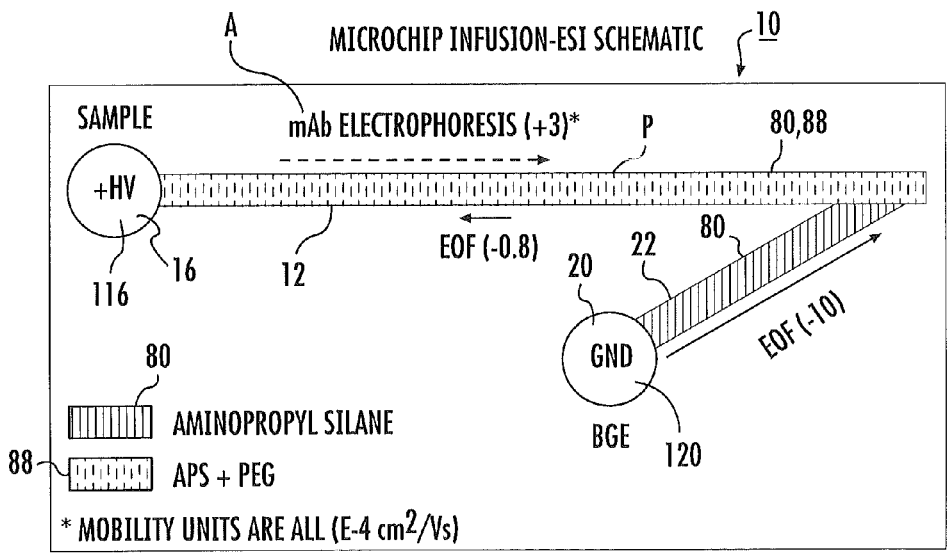
FIG. 1B is a schematic illustration of another exemplary fluidic device similar to that shown in FIG. 1A, but with a different electric input for the electric field according to embodiments of the present invention.

Referring to FIG. 1A, embodiments of the invention provide a fluidic device 10 (which can be a microfluidic chip device) with at least one sample separation flow column or channel 12 and at least one ESI interface 25, which is typically including a junction J of the separation channel 12 and a background electrolyte channel 22 proximate at least one ESI emitter 15. The analyte molecules "A" have sufficiently greater cationic electrophoretic mobilities than at least some of the other unwanted components of the sample. The separation column 12 is configured to have a low electroosmotic mobility so that analyte molecules "A" that have a greater cationic electrophoretic mobility can be constantly drawn out of a sample matrix by applying an electric field using electric inputs 116, 120 for applying a defined voltage, which may be high voltages (HV) e.g., HV1, HV2, for example. However, other lower voltages or electric field configurations can be used. A single sample (e.g., plug) in the sample reservoir 16 can be configured to generate a sufficient spray duration, such as, by way of example only, between about 2 minutes to several hours, typically at least 5 minutes of substantially stable spray or output from a respective emitter to a mass spectrometer to generate (summed) spectra data using a mass spectrometer. FIG. 1B illustrates that the electrical input 120 can be an electrical ground.

Figure 2:
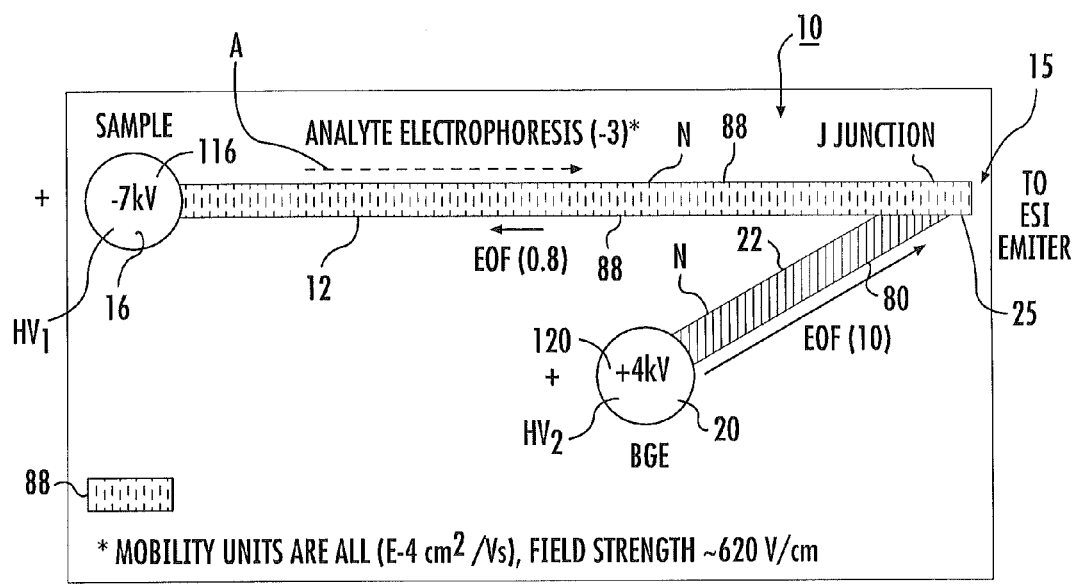
FIG. 2 is a schematic illustration of a fluidic device similar to that shown in FIG. 1 but with reverse EOF electrical charge configurations according to some embodiments of the present invention.

The devices 10, 10' (FIGS. 4A-4C) described herein are particularly useful for infusion-ESI to provide the integrated sample processing. In FIGS. 1A and 2, the arrows indicate the direction and relative magnitude of electroosmotic flow (EOF). In FIG. 1A, the dashed arrow indicates the direction that a highly mobile cation would migrate with a positive surface charge (anodic EOF) configuration of the channels 12, 22. The reverse applies to the embodiment of FIG. 2. The ESI interface 25 can be located at the far right end of the channel 12. The device 10 can include a sample reservoir 16 and a pump or background electrolyte (BGE) reservoir 20 with an associated channel 22. The at least one emitter 15 can generate a substantially constant spray plume 15p (FIG. 3A) or otherwise infuse the analyte "A" for collection onto a device for subsequent analysis or directly into an inlet region of a mass spectrometer 75 for generating spectra. The embodiments shown in FIGS. 1A, 1B use positive charge to generate the electrospray of the analyte A from the emitter(s) 15. The surfaces of the flow channels 12, 22 can have a positive charge "P" that can be provided by selection of the substrate material and/or coatings applied thereto.

Figure 3A:
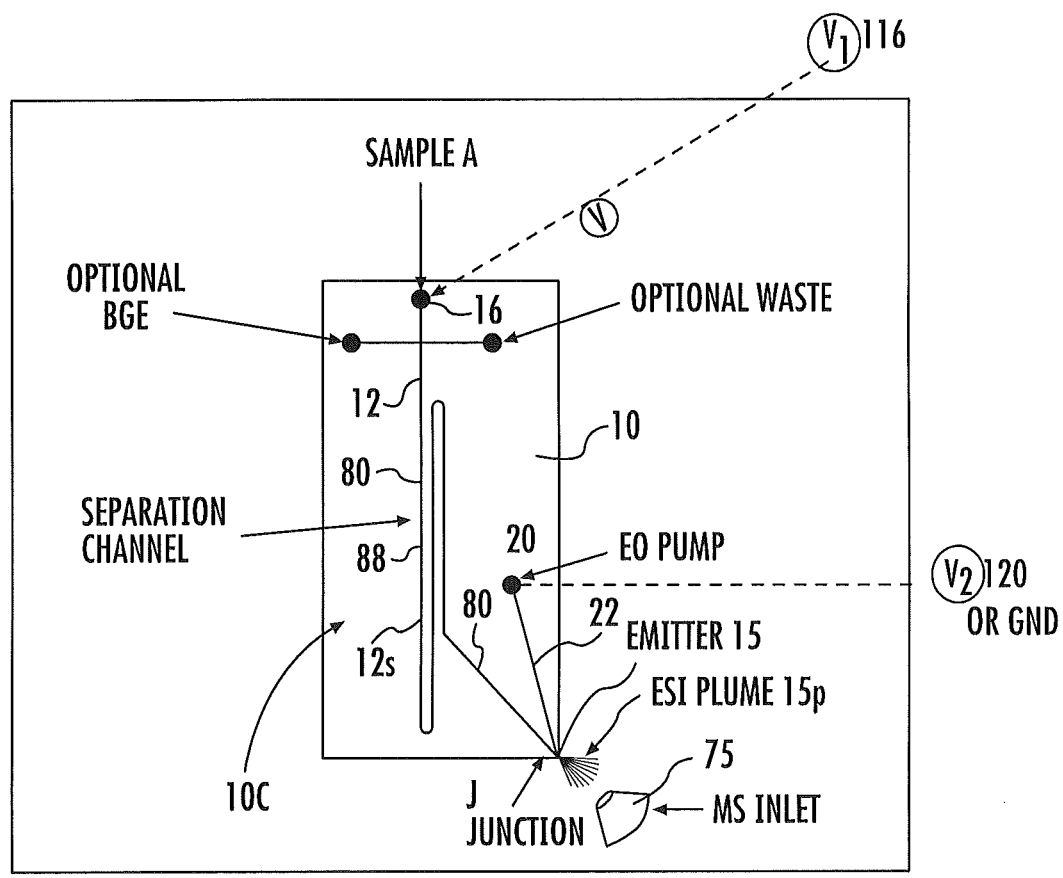
FIG. 3A is a schematic illustration of a microfluidic device according to embodiments of the present invention.
Figure 3B:
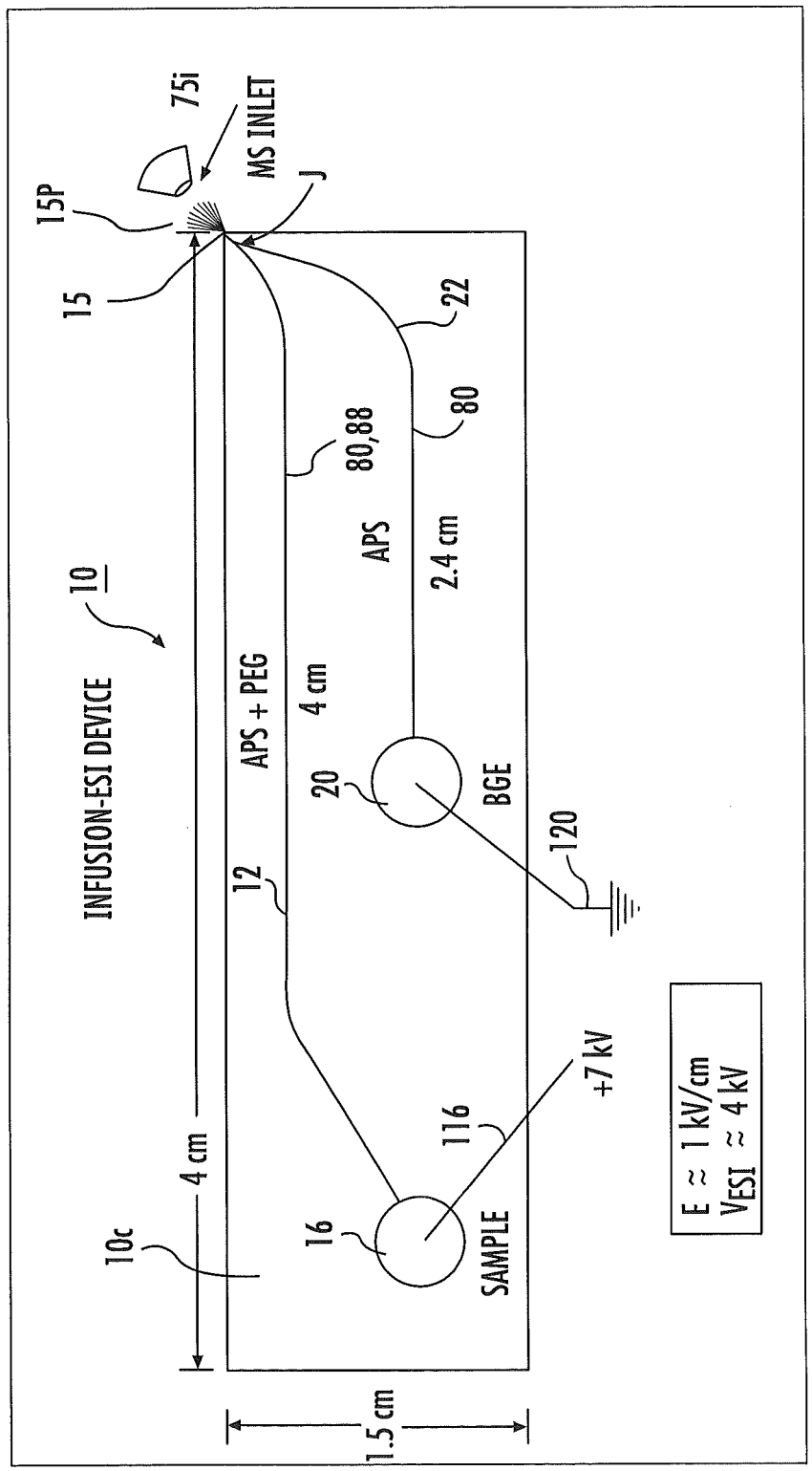
FIG. 3B is a schematic illustration of another microfluidic device according to embodiments of the present invention.
Figure 4A:
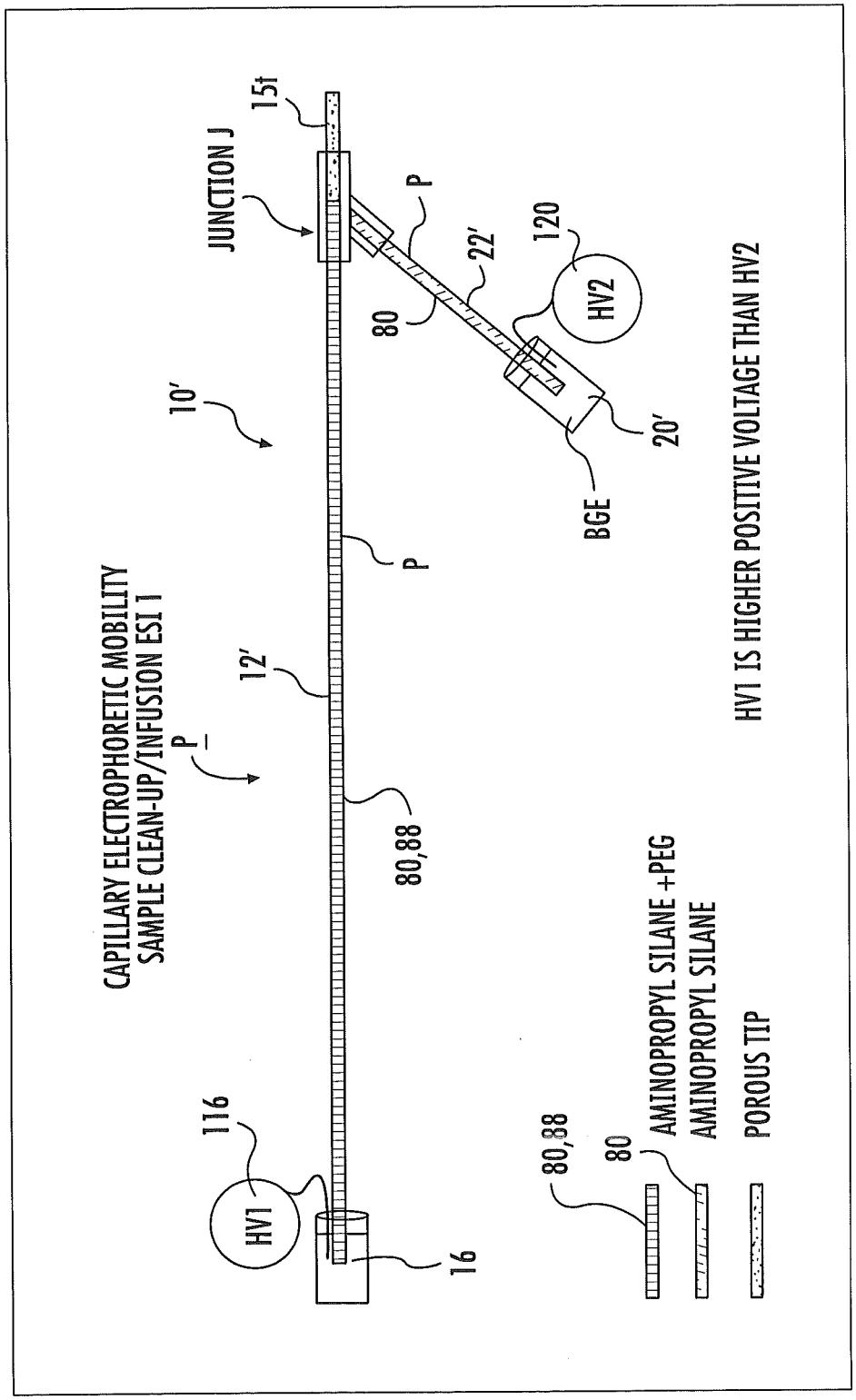
FIGS. 4A-4C are schematic illustrations of examples of capillary ESI systems with integrated online sample processing according to embodiments of the present invention.
Figure 4B:
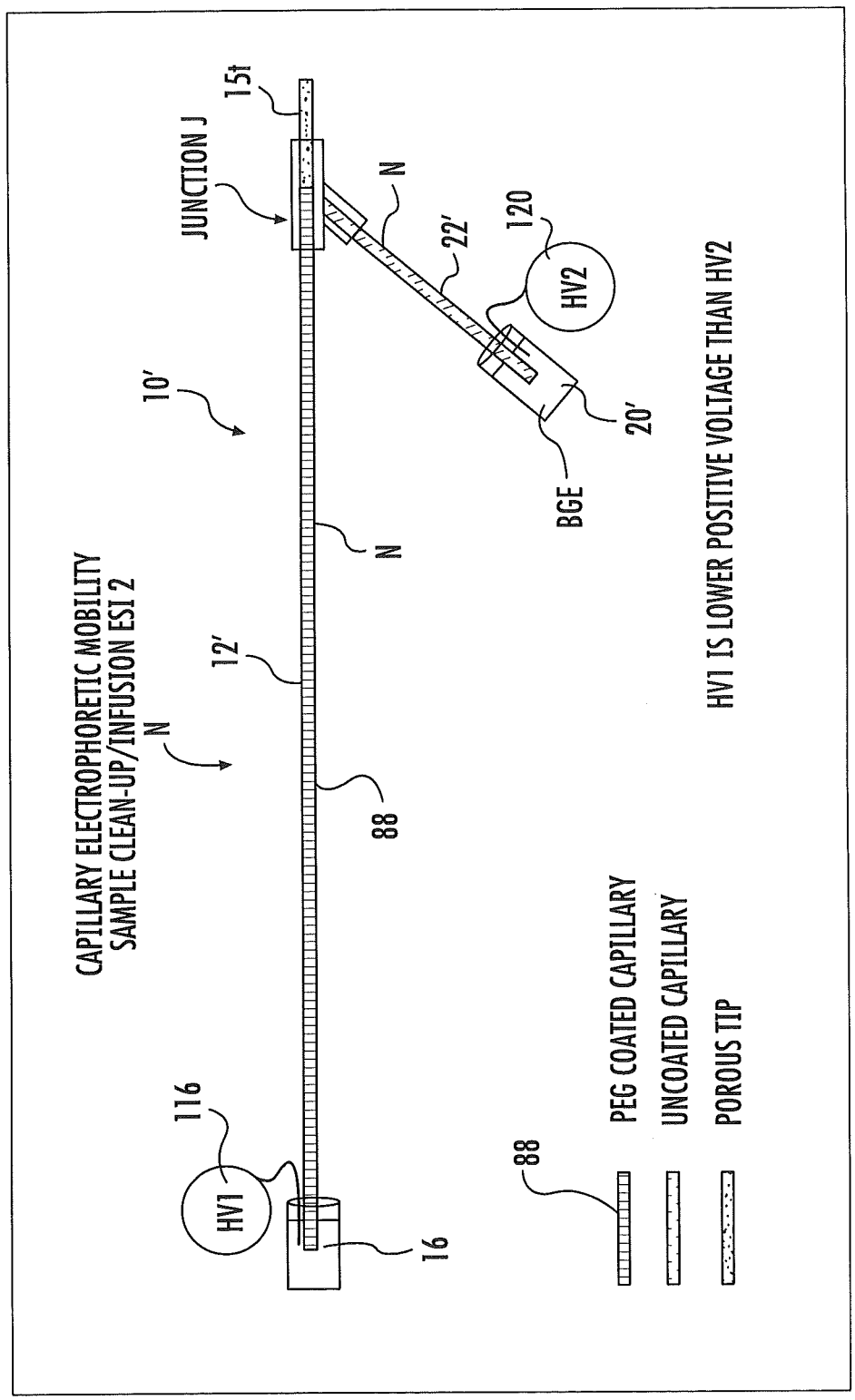
Figure 4C:
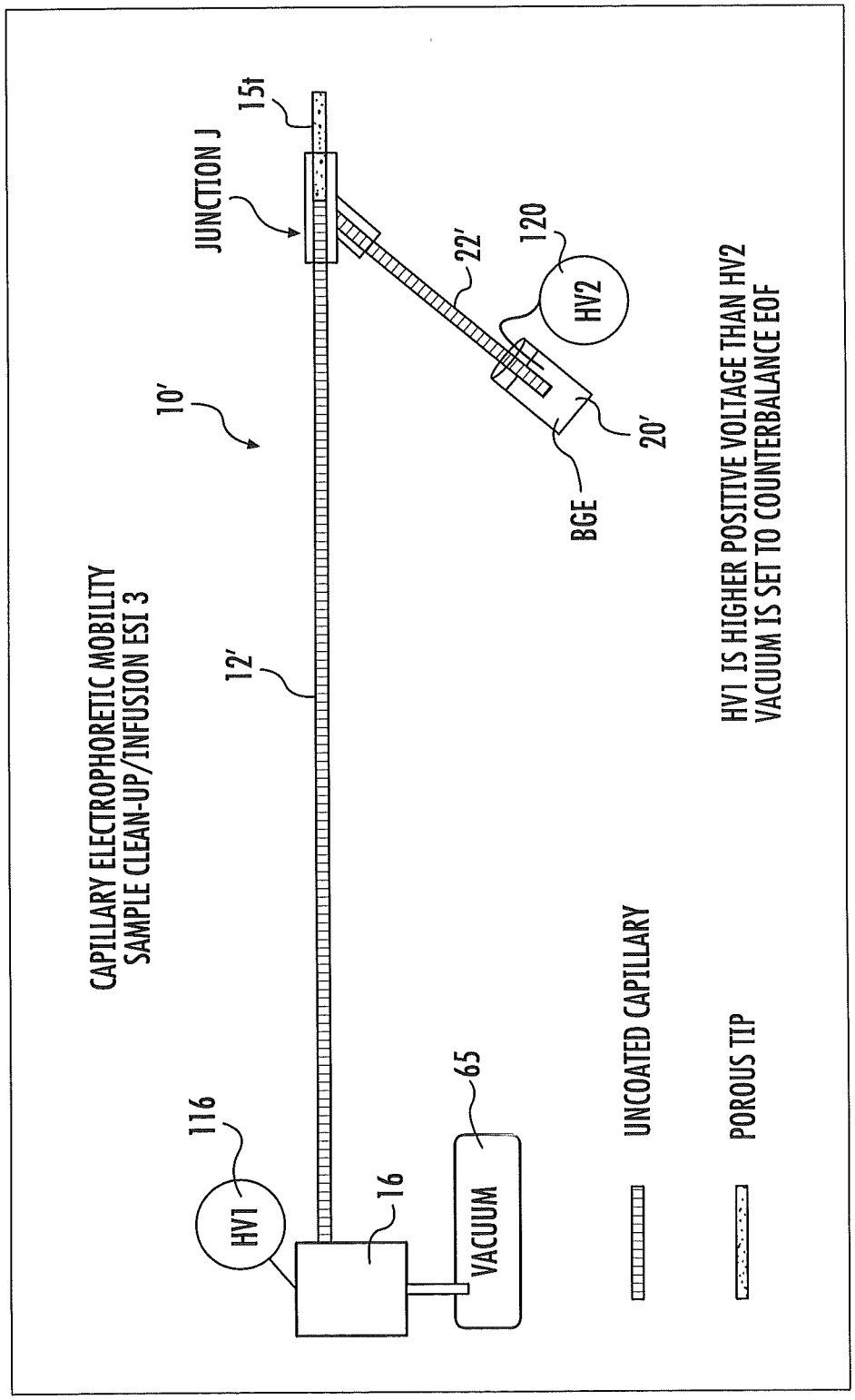

The differential axial transport can be implemented with a microfluidic device (FIGS. 1-3) or with capillary tubing and connectors, FIGS. 4A-4C.

FIG. 2 illustrates an embodiment similar to FIG. 1A, but with an anionic surface charge used to selectively transport the analyte A. In this embodiment, the channels 12, 22 can be formed of or include a coating that has a negative charge "N" and the analyte A may have a negative charge.

The sample reservoir 16 may be on the device 10 as shown or may reside upstream of the device 10 and be in fluid communication with the at least one separation channel 12. The BGE reservoir 20 can reside on the device or reside upstream of the device and be in fluid communication with the respective channel 22. The junction (J) may reside proximate the at least one emitter 15 on an outer edge or end of the device, typically between about 1-600 microns to reduce dead space/volumes.

FIGS. 1A and 1B are a simplified schematic of a device 10 with channels 12, 22. FIGS. 1A, 1B illustrate both of the channels 12, 22 with the positive charge coating 80 and channel 12 only with the reduced EOF coating 88. When an electric field is applied to this fluidic network, highly mobile cations of analyte "A" migrate or travel against the EOF in the separation channel 12 as indicated by the dashed arrow over the channel 12 toward the ESI interface 25. Low mobility cations, neutrals, and anions present in the sample matrix are excluded from the separation channel 12 (or at least from substantial movement through the channel) and typically remain in the sample reservoir 16.

The mismatch in EOF between the BGE or pump channel 22 and the separation channel 12 can, in some embodiments, also define an electroosmotic pump which drives fluid out of the device 10 through the at least one emitter 15 for ESI-MS.

In some embodiments, the sample separation channel 12 can have an electrical input 116 which is a voltage that is greater than the pump or BGE reservoir electrical input 120 (with both being positive or with the pump or BGE reservoir at ground). In other embodiments, the 116 voltage can be less than the input 120 (and both may be positive). The selected voltage differential can depend on the analyte being transported, the type of fluidic structure used to provide the flow, lengths, shapes and/or positions of the channels 12, 22 and the like.

One of the electric potentials 116, 120 applied can be a low voltage or even an electrical ground. The inputs 116, 120 can be selected to generate an electric field of proper magnitude and polarity for analyte migration and a suitable electrospray voltage. The magnitude of the electric field strength can depend on the application and microfluidic device. In the absence of pressure-driven flow, the electric field can determine the analyte migration velocity and the rate of bulk flow for supporting the electrospray plume. Pressure-driven flow can enhance or counter-balance either or both of these flows.

For capillary electrophoresis, typical field strengths usually range from about 100 V/cm to well over 1000 V/cm. For positive ESI, the electrospray voltage is usually between +1 and +5 kV, relative to the potential of the mass spectrometer inlet. On some instruments the mass spectrometer inlet 75i has a voltage that can be varied, while on other instruments it remains fixed near ground.

In some particular embodiments, the voltage differential between the input 116 and input 120 can be at least 20%, and even at least 50% greater. The electric inputs 116, 120 for applying the electric field can be located at other positions than those shown, such as proximate the respective reservoirs 16, 20 but upstream or downstream a distance thereof but in a position that applies the appropriate field and forms suitable EOFs.

The BGE or pump reservoir 20 can hold any suitable background electrolyte fluid appropriate for the target analyte(s) A and electrospray output as is known to those of skill in the art. For positive biased devices/systems such as shown in FIGS. 1A, 1B a weak acid may be used such as an acetonitrile and formic acid solution. However, other background electrolyte fluids can be used as is well known. For a negative biased system/device such as shown in FIG. 2, a basic pH electrolyte can be used.

The EO pump 22 for electrospray ionization can take forms other than shown in FIGS. 1-3. The EO pump can be described as the side channel 22 with appropriately designed surface chemistry to create a desired EO flow (with reservoir 20 forming a pump reservoir). The basic requirement is to have two channels intersect at a junction ("J"), which may be a T-like or V-like junction (not restricted to a right angle intersection). Voltage is applied to two of the three resulting channel termini generating an axial electric field through the associated channel segments. To realize hydraulic transport through the third channel segment, the electroosmotic mobility in the two channel segments that contain the axial electric field have a different magnitude.

The difference in electroosmotic mobility can be achieved by chemically modifying one, or both, of the associated channel segments so as to produce different surface charge densities and hence different electroosmotic mobilities. Electroosmotic mobility can also be modified by coating a channel wall with electrically neutral polymer films, thereby increasing the effective fluid viscosity within the electrical double layer at the wall. Another way to modify electroosmotic mobility is reduce one of the channel lateral dimensions to distances similar in magnitude to the Debye length of the solution being electroosmotically pumped. The described methods for modifying electroosmotic mobility may also be used in combination, where desired. Exemplary methods for electroosmotic pumping are further described in U.S. Pat. No. 6,110,343, the contents of which are hereby incorporated by reference as if recited in full herein.

For positive mobility bias embodiments, such as shown in FIGS. 1A, 1B at least the surfaces of the separation channel and BGE or pump channel 12, 22, respectively, can be configured with a suitable substrate and/or covalently modified with a suitable coating 80 to provide a desired positive charge "P" as will be discussed further below. The coating 80 or channel substrate material of each channel 12, 22 can be the same (typically the same and provided as a monolayer) or different to provide a strong positive charge on all of the channel surfaces and therefore a strong anodic EOF.

For the negative bias embodiments, such as shown in FIG. 2, at least the surfaces of the separation and BGE or pump channel 12, 22 can be configured with a negative charge based on the substrate material used and/or a coating applied thereto for a strong cathodic EOF. Again, the same material or coating(s) may be used or a different substrate material and/or coating can be used to generate the negative charge. For example, a glass substrate defining the channels 12, 22 can provide a negative surface charge N.

Surface charge and ion migration direction can be such that if the surface charge is negative (cathodic EOF), cations will migrate in the same direction as the EOF. If the surface charge is positive (anodic EOF), anions will migrate in the same direction as the EOF.

The separation channel 12 can be modified to reduce EOF relative to the other channel 22 by a desired amount using an EOF reduction coating material 88 such as a viscous polymer. The differential in EOF can typically be at least about 20% but the surfaces of the channels 12, 22 can be configured to provide less or more EOF differential. As shown in FIGS. 1A and 2, in a relative measure, the channel 22 can have an EOF of (−10/+10) while the channel 12 can have an EOF of about (−0.8/+0.8). However, the EOF differential can vary depending on a number of factors FIG. 3A is a schematic illustration of another embodiment of the invention. The device 10 can be a microfluidic chip 10c formed with stacked hard and/or soft substrates 11 (FIGS. 5A-5C) with integrated microfluidic channels 12, 22.

For CE separations, the cross structure shown in FIG. 3A is typically used for electrokinetically-gating sample plugs into the separation channel. For infusion-ESI methods or uses, such as that contemplated by embodiments of the invention, the cross structure is not necessary and the reservoirs labeled BGE and waste in FIG. 3A are not used and/or may be omitted from the device 10.

FIG. 3B illustrates another embodiment of the device 10 which can be implemented as a fluidic microchip 10c. The separation channel 12 can be curvilinear with straight segments that reach from one short side of the chip to another where the emitter 15 is located so that the plume 15p of the analyte for the ESI output toward an MS inlet 75i, according to some embodiments of the invention. As with FIGS. 1A, 1B and 2, FIGS. 3A and 3B show that the device 10 can include at least one emitter 15, at least one separation channel 12 and at least one pump channel 20. Examples of hard or substantially rigid materials include, but are not limited to, substrates comprising one or combinations of: glass, quartz, silicon, ceramic, silicon nitride, polycarbonate, and polymethylmethacrylate. In particular embodiments, the device 10 can include a glass substrate such as a borosilicate. In other embodiments, a rigid polymer material may be used to form the microchip. The device 10 can also include one or more layers of a soft or flexible substrate. Soft substrate materials, where used, can have a low Young's Modulus value. For example, elastomers and harder plastics and/or polymers can have a range between about 0.1-3000 MPa. Examples of soft materials include, but are not limited to, polydimethylsiloxane (PDMS), polymethylmethacrylate (PMMA), and polyurethane. See, e.g., co-pending PCT/US2012/027662 filed Mar. 5, 2012 and PCT/US2011/052127 filed Sep. 19, 2011 for a description of examples of microfabricated fluidic devices. See, also. Mellors, J. S.; Gorbounov, V.; Ramsey, R. S.; Ramsey, J. M., Fully integrated glass microfluidic device for performing high-efficiency capillary electrophoresis and electrospray ionization mass spectrometry. *Anal Chem* 2008, 80 (18), 6881-6887. For additional information that may be useful for some designs, see also, Xue Q, Foret F, Dunayevskiy Y M, Zavracky P M, McGruer N E & Karger B L (1997), Multichannel Microchip Electrospray Mass Spectrometry. *Anal Chem* 69, 426-430, Ramsey R S & Ramsey J M (1997), Generating Electrospray from Microchip Devices Using Electroosmotic Pumping. *Anal Chem* 69, 1174-1178, Chambers A G, Mellors J S, Henley W H & Ramsey J M (2011), Monolithic Integration of Two-Dimensional Liquid Chromatography—Capillary Electrophoresis and Electrospray Ionization on a Microfluidic Device. *Analytical Chemistry* 83, 842-849. The contents of these documents are hereby incorporated by reference as if recited in full herein.

FIG. 3A also illustrates that the separation channel 12 can be a serpentine or curvilinear flow channel 12s and that the at least one emitter 15 is on a tip of the chip 10c, However, straight, angled or other configurations of the channel 12 may be used and the emitter(s) 15 can be in other locations.

Figure 5A:
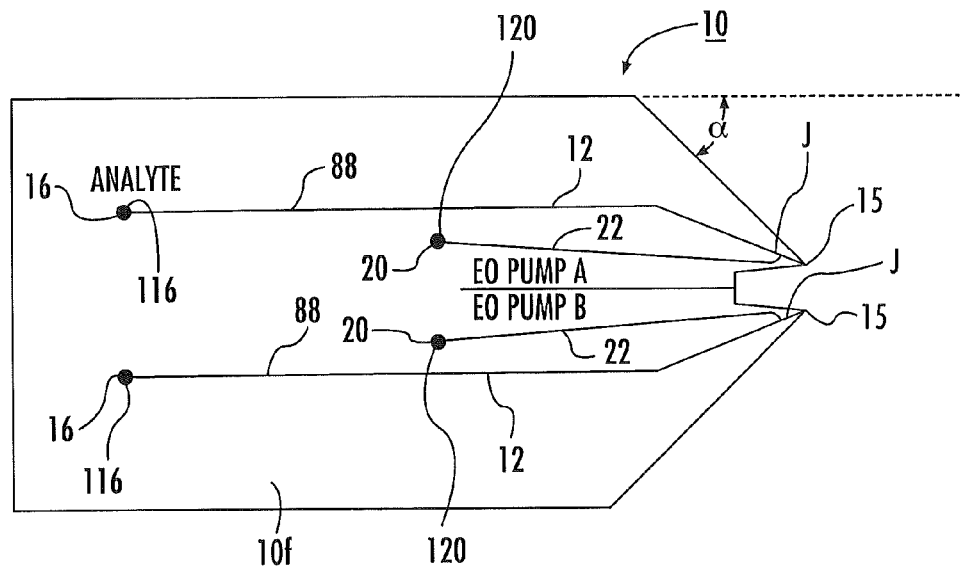
FIG. 5A is a top view of an example of a microfluidic device with online integrated sample processing (e.g., cleanup) capability according to other embodiments of the present invention.
Figure 5B:
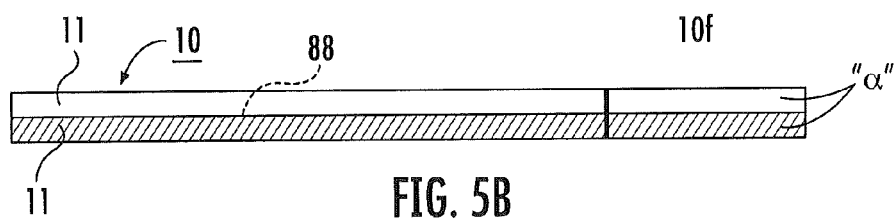
FIG. 5B is a (long) side view and FIG. 5C is an end view (e.g., short side) of the microfluidic device shown in FIG. 5A according to embodiments of the present invention.
Figure 5C:
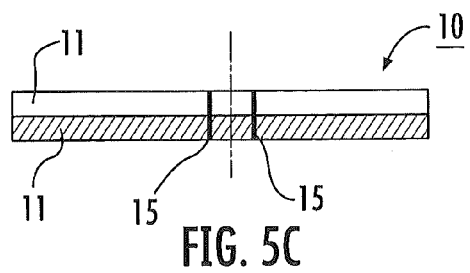

FIGS. 5A-5C illustrate an example of a device 10 with a plurality of separation channels 12 and pump channels 20. A plurality of emitters 15 are also shown. However, it is also contemplated that each channel 12 can communicate with a common emitter as well (not shown). The device 10 can be operated so that each emitter concurrently or serially discharges (sprays) the analyte A. FIGS. 5B and 5C illustrate two stacked substrates 11 that form the enclosed channels 12, 20. The electrical inputs 116, 120 can be applied using a switch from a common power supply or each may have a dedicated power input (not shown).

FIGS. 4A-4C are schematic illustrations of capillary devices 10' using electrophoretic-mobility based sample clean-up/infusion ESI. As shown, the devices 10' can employ a porous tip emitter 15t capillary setup, but they could be applied with other CE-MS type emitters/setup (e.g., concentric sheath flow, microchip and the like). As also shown, the devices 10' include a capillary separation channel 12' and a BGE channel 22', each connected to a HV1, HV2 source and meeting at a junction J proximate the emitter 15t similar to the embodiments discussed above. However, instead of on an EO pump, capillary driven flow is used. Again, the channel surfaces can be configured to have the desired polarity (charge) and EOF mobility characteristics.

FIG. 4A illustrates that the separation channel 12' and the BGE channel 22' can each have a positive charge "P" that can be generated by a coating 80 and with a channel 12' with a reduced mobility EOF coating 88 to provide a reduced EOF relative to channel 22'. The device 10' can operate with HV1 having a greater positive voltage than HV2.

FIG. 4B illustrates that the device 10' can be configured with a negative charge "N" and the substrate forming the surfaces of the channels 12', 22' can have a negative charge as discussed with respect to FIG. 2 above. The channel 12' can also include coating 88. The device 10' can operate with HV1 having a lower positive voltage than HV2.

FIG. 4C illustrates that the capillary system 10' can also include a vacuum 65 applied to the capillary input. The HV1 can have greater positive voltage than the HV2 and the vacuum can be operated to counterbalance EOF. No special coatings are required and the capillaries forming the channels 12', 22' can be uncoated.

As discussed above, in some embodiments, the channels 12, 22 and 12', 22' can be configured with a material or materials (substrate and/or coating) to have a desired polarity or charge. In some embodiments, the channels 12, 22 and 12', 22' can be configured with a coating to provide the desired polarity or charge. A coating can be dynamic or static. Dynamic coatings generally do not adhere strongly to the channel wall and to maintain a stable dynamic coating, dynamic coating reagents are added to the background electrolyte, thus allowing the coating to be continuously regenerated. Exemplary dynamic coatings include, but are not limited to, neutral polymer coatings (e.g., hydroxypropyl methylcellulose coatings) and EOTrol™ coatings commercially available from Target Discovery of Palo Alto, Calif. Static coatings can be covalently bound to the channel wall or strongly adhered to the channel wall by noncovalent interactions (e.g., electrostatic interactions). Exemplary covalent static coatings include, but are not limited to, coatings formed using silane and/or silane reagents such as aminopropyltriethoxysilane, mercaptopropyltrimethoxysilane, polyethylene glycol (PEG) silane. Silane and/or silane reagents can be used to functionalize the surface of the channel wall and/or can act as a base layer for further modification(s). Exemplary noncovalent static coatings include, but are not limited, coatings comprising polymers including ionic polymers, ionic polymer multilayers and/or polyelectrolytes such as polyamines (e.g., PolyE-323 a polyamine that interacts with surface silanols by electrostatic and hydrogen bonding forces and yields a stable positive surface charge over a wide pH range), and polybrene polymers (e.g., polybrene—poly(vinyl sulfonic acid) polymers and polybrene—dextran sulfate—polybrene polymers). Other polymer coatings may be used such as cross-linked poly(vinyl alcohol).

For positive charge channels 12, 22, suitable coatings 80 include, for example, but are not limited to, aminopropyltriethoxysilane coatings, PolyE-323 coatings, and Polybrene—dextran sulfate—polybrene coatings.

For negative charge channels 12, 22 glass substrate channels may be used. Glass substrates do not require additional coatings, but may be coated to provide greater or more stable negative charge. However, if other substrates are used, aluminosilcate coatings or other negative charge coatings can be used including, for example, mercaptopropyltrimethoxysilane coatings and Polybrene—poly(vinyl sulfonic acid) coatings.

The separation channel 12, 12' (but not the BGE or pump channel 22, 22') can comprise a coating 88 selected to lower the anodic or cathodic based EOF in the separation channel 12, 12' relative to the corresponding anodic or cathodic EOF in the BGE or pump channel 22, 22'. This EOF differential can be in any suitable amount and can vary depending on the target analyte, the sample under analysis, the degree of sample cleaning desired, the length of the channels and the like. In some particular embodiments, the separation channel 12, 12' can have at least a 20% lower EOF (in mobility units E-4 $cm^2$/Vs) than the BGE or pump channel 22, 22'. In some embodiments, the EOF in the separation channel 12, 12' can be about 5× to at least 10× lower than the EOF in the other channel 22, 22'.

The EOF reduction coating 88 may be an overcoat on an underlying monolayer of a material providing a desired polarity, e.g., on a first ionic monolayer coating or placed directly on a channel substrate. The coating can be covalently bonded to an underlying coating or substrate. The coating can be non-covalently bonded to an underlying coating or substrate. The EOF reduction can be provided as a securely attached material layer and configured to provide a viscous or flow retardant surface. In some particular embodiments, the anodic or cathodic EOF in the separation channel 12 can be about 1E-04 $cm^2$/Vs or less.

The EOF reduction coating 88 can comprise poly(ethylene glycol) (PEG), which may be covalently attached to the first coating on the separation channel or directly on the separation channel substrate. In some embodiments, this PEGylation can lower the anodic EOF in the separation channel 12 from about 10E-04 $cm^2$/Vs for an unmodified first coating (APS) surface (such as may be in the BGE or pump channel 22), to less than about 1E-04 $cm^2$/Vs.

Figure 6:
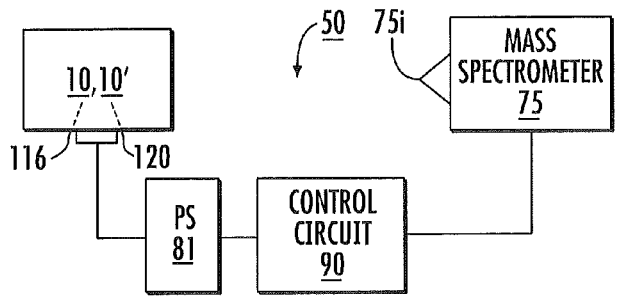
FIG. 6 is a block diagram of a system which includes at least one fluidic device configured for online sample processing using differential axial transport in cooperating communication with a mass spectrometer according to embodiments of the present invention.

FIG. 6 illustrates a system 50 with a mass spectrometer 75 with an inlet orifice 75$i$ in communication with at least one fluidic device 10, 10'. The mass spectrometer 75 can generate spectra using a plume sprayed from one or more emitters 15. In some embodiments, the microchip 10, 10' can be configured to spray both an analyte and a reference material from a separate ESI emitter (not shown). FIG. 6 also illustrates that an analyzer system 50 that may include a control circuit 90 in communication with the mass spectrometer 75 and fluidic device 10, 10' and at least one power supply 81 in communication with the electrical inputs 116, 120 on the fluidic device 10, 10'. The control circuit 90 can synchronize fluid transport through the fluidic device 10, 10' with data acquisition by the mass spectrometer 75. The control circuit 90 may cause different emitters (where used) to sequentially spray or spray concurrently.

In some embodiments, the devices 10, 10' can be used for deposition onto a target receiving substrate for subsequent analysis. For example, the devices 10, 10' can spray or emit fluid from one or more ESI emitters onto a planar substrate for subsequent analysis by Matrix-assisted laser desorption/ionization (MALDI). See, e.g., Morozov V N (2010) Electrospray Deposition of Biomolecules. In *Nano/Micro Biotechnology*, pp. 115-162 and Hensel R R, King R C & Owens K G (1997), Electrospray sample preparation for improved quantitation in matrix-assisted laser desorption/ionization time-of-flight mass spectrometry, *Rapid Communications in Mass Spectrometry* 11, 1785-1793. MALDI is one of the two "soft" ionization techniques besides electrospray ionization (ESI) that allow for the sensitive detection of large, non-volatile and labile molecules by mass spectrometry. MALDI has developed into an indispensable tool in analytical chemistry, and in analytical biochemistry in particular.

Figure 7:
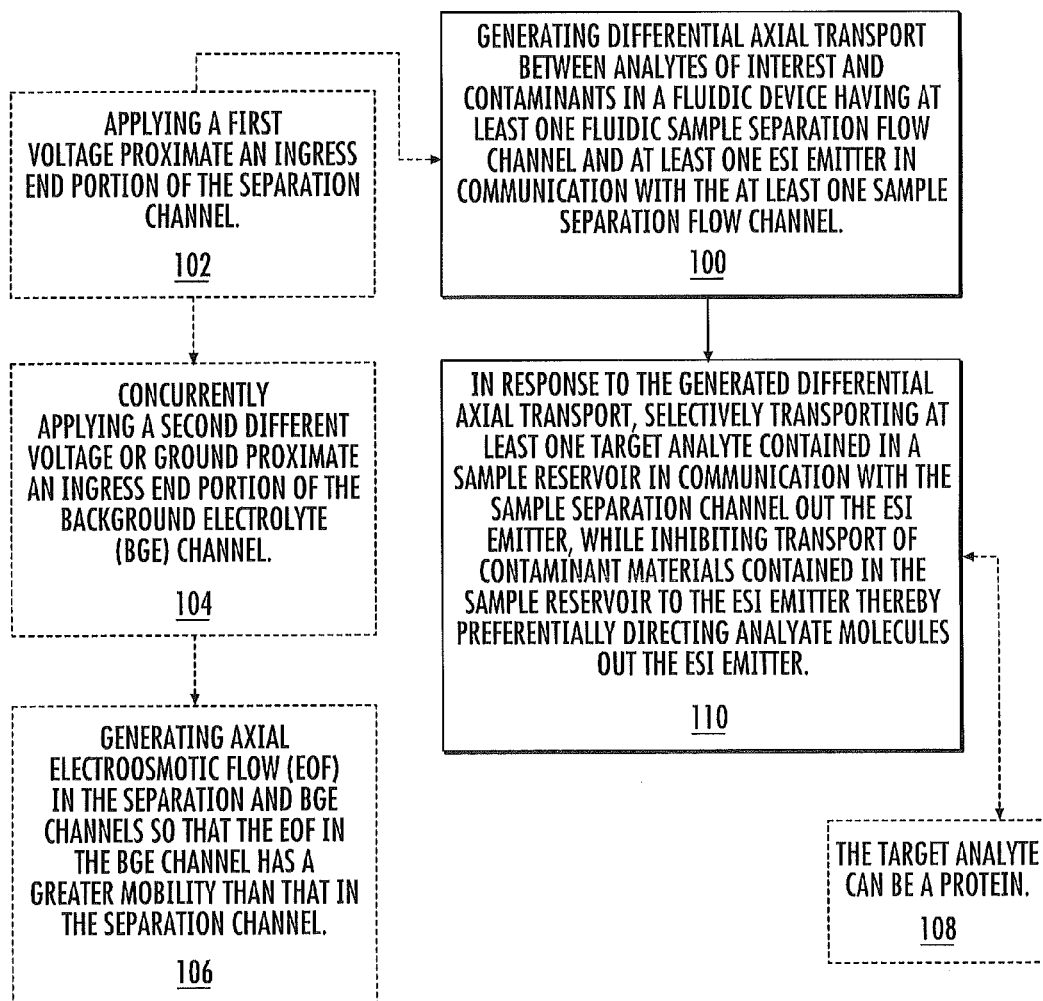
FIG. 7 is a flow chart of exemplary operations that can be used to carry out embodiments of the present invention.

FIG. 7 illustrates exemplary operations that can be used to carry out embodiments of the invention. Differential axial transport between analytes of interest and contaminants can be generated in a fluidic device having at least one fluidic sample separation flow channel and at least one ESI emitter in communication with the at least one sample separation flow channel (block 100). In response to the generated differential axial transport, at least one target analyte contained in the sample reservoir is selectively transported out the ESI emitter, while inhibiting transport of contaminant materials contained in the sample reservoir to the ESI emitter thereby preferentially directing analyte molecules out the ESI emitter (block 110).

In some embodiments, the differential axial transport can be generated by applying a first voltage proximate an ingress end portion of the separation channel (block 102) and concurrently applying a second different voltage or ground proximate an ingress end portion of the background electrolyte (BGE) channel (block 104). Axial electroosmotic flow (EOF) is generated in the separation and BGE channels in response to the application of the voltage/electric field so that the EOF in the BGE channel has a greater mobility than that in the separation channel (block 106).

The target analyte can be a biomolecule such as an intact protein (block 108).

Embodiments of the invention allow dirty samples to be analyzed by electrospray mass spectrometry with integrated online sample processing (e.g., clean-up) with relatively non-complex instrumentation. The sample can be substantially continuously infused for at least 30 seconds, typically between 1 minute to about 2 hours or even longer, more typically between about 2-60 minutes. The composition of the background electrolyte can be varied without retention/elution of the sample from a chromatographic bed associated with online desalting methods that use a liquid chromatography column coupled to an electrospray interface.

The present invention is explained in greater detail in the following non-limiting Examples.

EXAMPLES

Example 1

Figure 8:
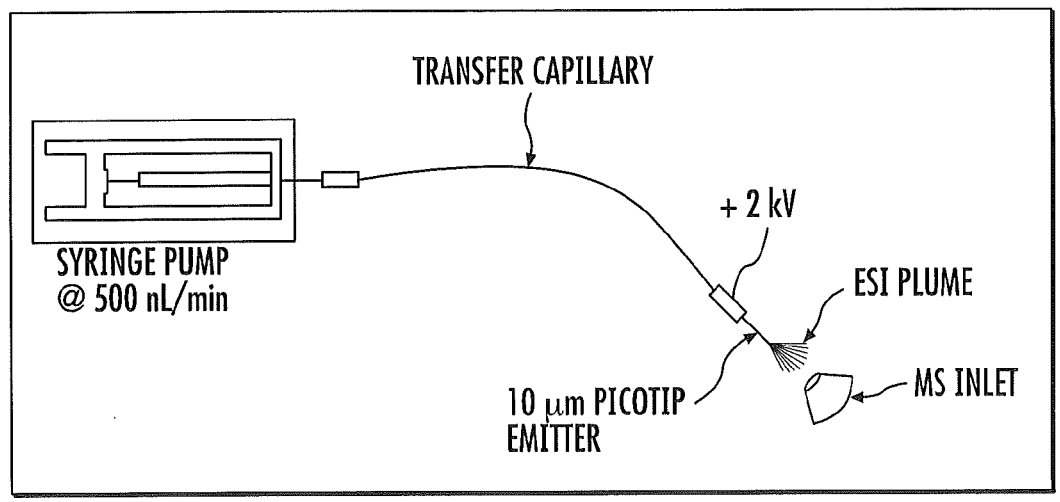
FIG. 8 is a schematic illustration of a prior art syringe pump infusion-ESI system used to generate data shown in FIGS. 9A and 9B.

To evaluate the performance of a prototype device, a conventional syringe pump infusion system (FIG. 8) was used to perform ESI-MS of two intact monoclonal antibody (mAb) samples. The transfer capillary was fused silica with a 100 µm inner diameter. The capillary spray tip had a tapered tip with a 10 µm inner diameter. The ESI voltage was applied to the stainless steel union that connected the ESI emitter to the transfer capillary.

The first sample was purified by washing with background electrolyte (BGE) three times on a 10 kDa molecular weight cutoff (MWCO) filter. The BGE was a mixture of water with 50% acetonitrile and 0.1% formic acid by volume. After washing, the sample was diluted to 4 mg/mL with BGE. The second sample was prepared by diluting the raw (20 mg/mL) formulation to a concentration of 2 mg/mL with BGE. Each sample was infused through the system for about 15 minutes, A summation of about 5 minutes of ESI-MS data was used to generate a mass spectrum for each sample.

Figure 9A:
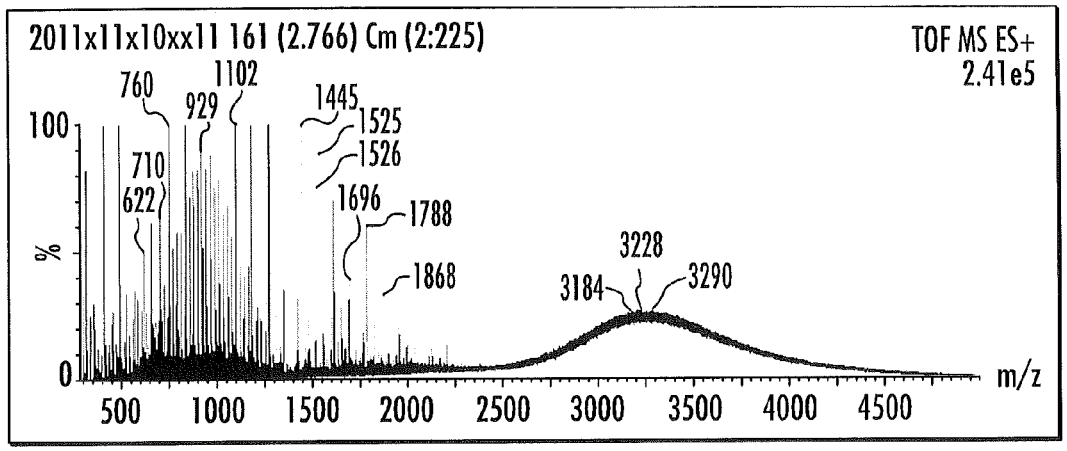
FIGS. 9A and 9B are graphs of spectra, intensity (percentage) versus m/z of about 5 minutes of summed mass spectra associated with the device shown in FIG. 8.
Figure 9B:
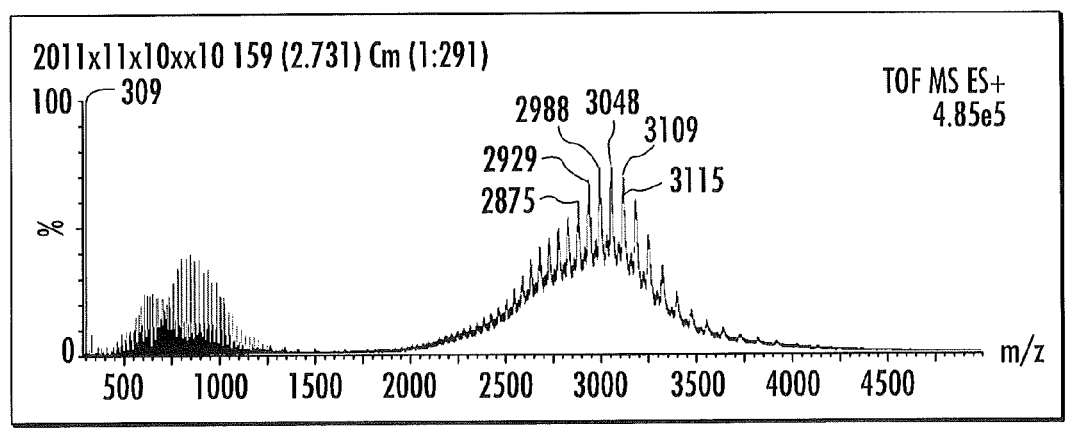

FIG. 9 shows that the MWCO purified sample yielded a convoluted protein envelope centered near 3000 m/z along with a significant amount of surfactant peaks between 500 and 1500 m/z. Analysis of this spectrum would yield only a rough estimate of the average molecular weight of the mAb. The sample diluted from the raw formulation yielded an uninterpretable broad peak in the baseline where the mAb charge state envelope should be, along with a tremendous amount of background signal ranging up to about 2000 m/z. The bottom spectrum (FIG. 9B) was obtained using the mAb sample washed three times on a 10 kDa MWCO filter. The top spectrum (FIG. 9A) was obtained using the mAb sample diluted from the raw formulation.

The same two samples run on the syringe pump system were also run on a prototype microfluidic system such as the one shown in FIG. 3A. The device 10 was fabricated in glass substrates using previously reported methods. See, Mellors, J. S.; Gorbounov, V.; Ramsey, R. S.; Ramsey, J. M., Fully integrated glass microfluidic device for performing high-efficiency capillary electrophoresis and electrospray ionization mass spectrometry. *Anal Chem* 2008, 80 (18), 6881-6887. All surfaces of the device were covalently modified with an aminopropyl silane (APS) reagent. This results in a strong positive charge on all of the channel surfaces and therefore a strong anodic EOF. All channels except the EO pump channel were then modified by covalently attaching poly(ethylene glycol) (PEG). This PEGylation lowered the anodic EOF from approximately 10E-04 $cm^2/Vs$ for an unmodified APS surface, to less than 1E-04 $cm^2/Vs$.

Figure 10A:
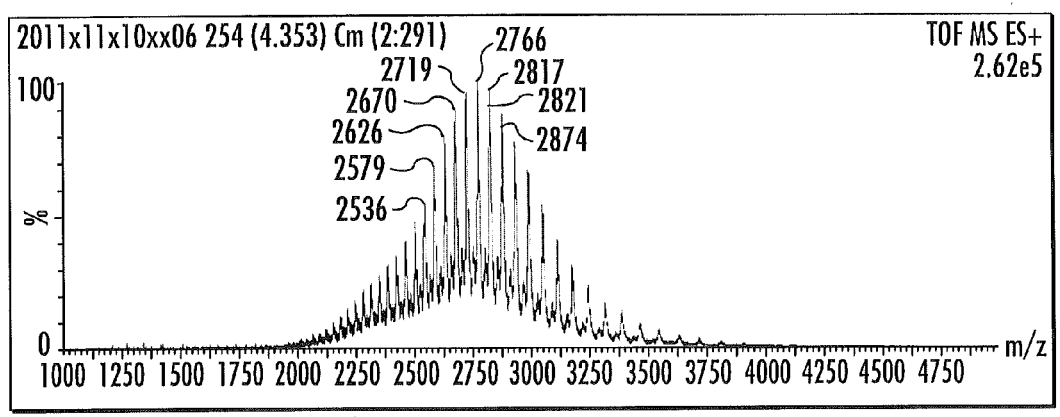
FIGS. 10A and 10B are graphs of spectra, intensity (percentage) versus m/z of about 5 minutes of summed mass spectra associated with the device shown in FIG. 3A having integrated online sample clean up according to embodiments of the present invention.
Figure 10B:
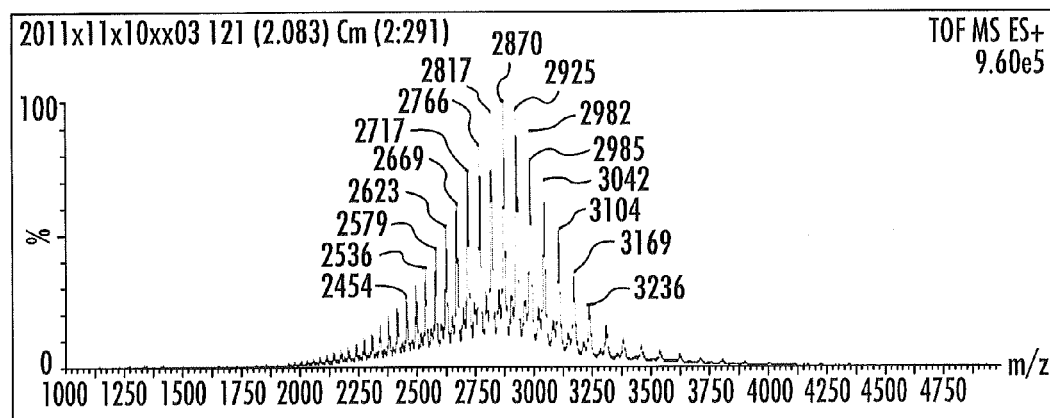
Figure 11:
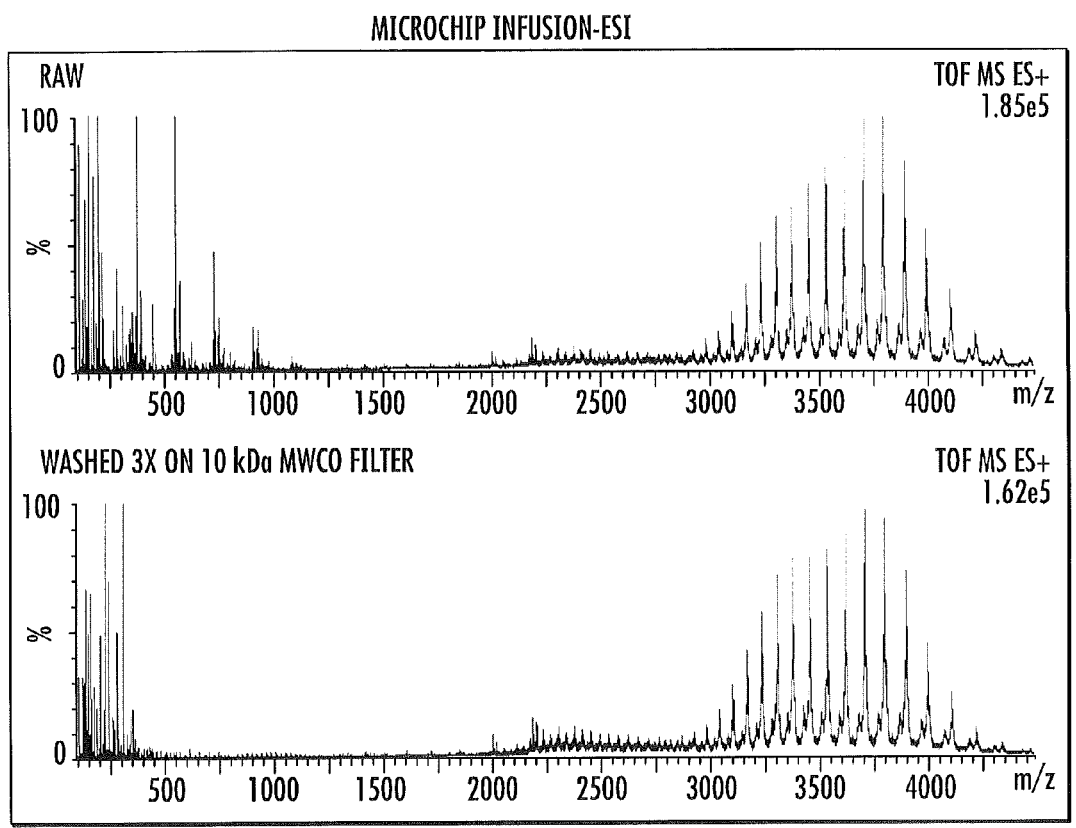
FIGS. 11-16 are graphs of additional experimental data obtained using differential axial transport between a target analyte and contaminate materials according to embodiments of the present invention.

The channels 12, 22 of the microfluidic device 10 were first filled with BGE (50% acetonitrile, 0.1% formic acid) then one of the samples was loaded into the sample reservoir 16 (FIG. 3A). When +13 kV was applied to the sample reservoir 16 and +2 kV was applied to the EO pump reservoir 20 a stable electrospray plume was generated. After about 2 minutes a clean MS spectrum was observed. The ESI-MS signal was very stable for over 15 minutes. Again, about a 5 minute summation was used to generate a mass spectrum for each of the samples. FIG. 10 shows that both samples yielded clean spectra with charge state envelopes centered around 2800 m/z. No surfactant ions were observed for either sample. Analysis of either of these spectra would yield relatively accurate molecular weight estimates of several mAb variants present in the sample. The bottom spectrum (FIG. 10B) was obtained using the mAb sample washed three times on a 10 kDa MWCO filter. The top spectrum (FIG. 10A) was obtained using the mAb sample diluted from the raw formulation.

These results clearly demonstrate that online sample processing using differences in electrophoretic mobility is an effective method for generating high quality ESI-MS data using dirty samples. This method could be applied to a number of different applications.

Example 2

To produce the desired EOF, which can differ depending on the application, one or more coatings may be used in the prototype device 10 described in Example 1 or other suitable fluidic device configurations to modify one or more surfaces of the device. For example, one or more of the following coatings may be used to modify one or more surfaces of the device 10, 10'. A hydroxypropyl methylcellulose coating may be used to reduce the EOF. An EOTrol™ coating may be used to optimize the EOF by providing a coating that is nearly pH- and buffer-independent. An aminopropyltriethoxysilane coating may be used to provide a strong positive charge over a wide pH range and/or to provide a base layer for additional surface modification (e.g., bonding of NHS-PEG).

A mercaptopropyltrimethoxysilane coating may be used to provide a strong negative charge over a wide pH range and/or as a base layer for additional surface modification. A PEG silane coating may be used for direct attachment of PEG to surface silanols without a base layer. A PolyE-323 coating may be used to provide a stable positive surface charge over a wide pH range. A polybrene—poly(vinyl sulfonic acid) coating, which comprises a double layer where cationic polybrene interacts electrostatically with surface silanols and anionic poly(vinyl sulfonic acid) interacts electrostatically with polybrene, may be used to provide a stable negatively charged surface. A polybrene—dextran sulfate—polybrene coating, which comprises a triple layer coating, may be used to provide a positively charged surface. A cross-linked poly(vinyl alcohol) coating may be used to provide a neutral hydrophilic surface.

Alternatively and/or in addition to, pressure could be applied to the sample reservoir 16 to produce the desired EOF. For example, a positive or negative (vacuum) pressure could be applied to the sample reservoir 16 to increase or decrease the EOF. In such a system a pressure regulator could be used to "tune" the flow to a level that allows only the analyte(s) of interest to reach the ESI interface.

Example 3

Figure 12:
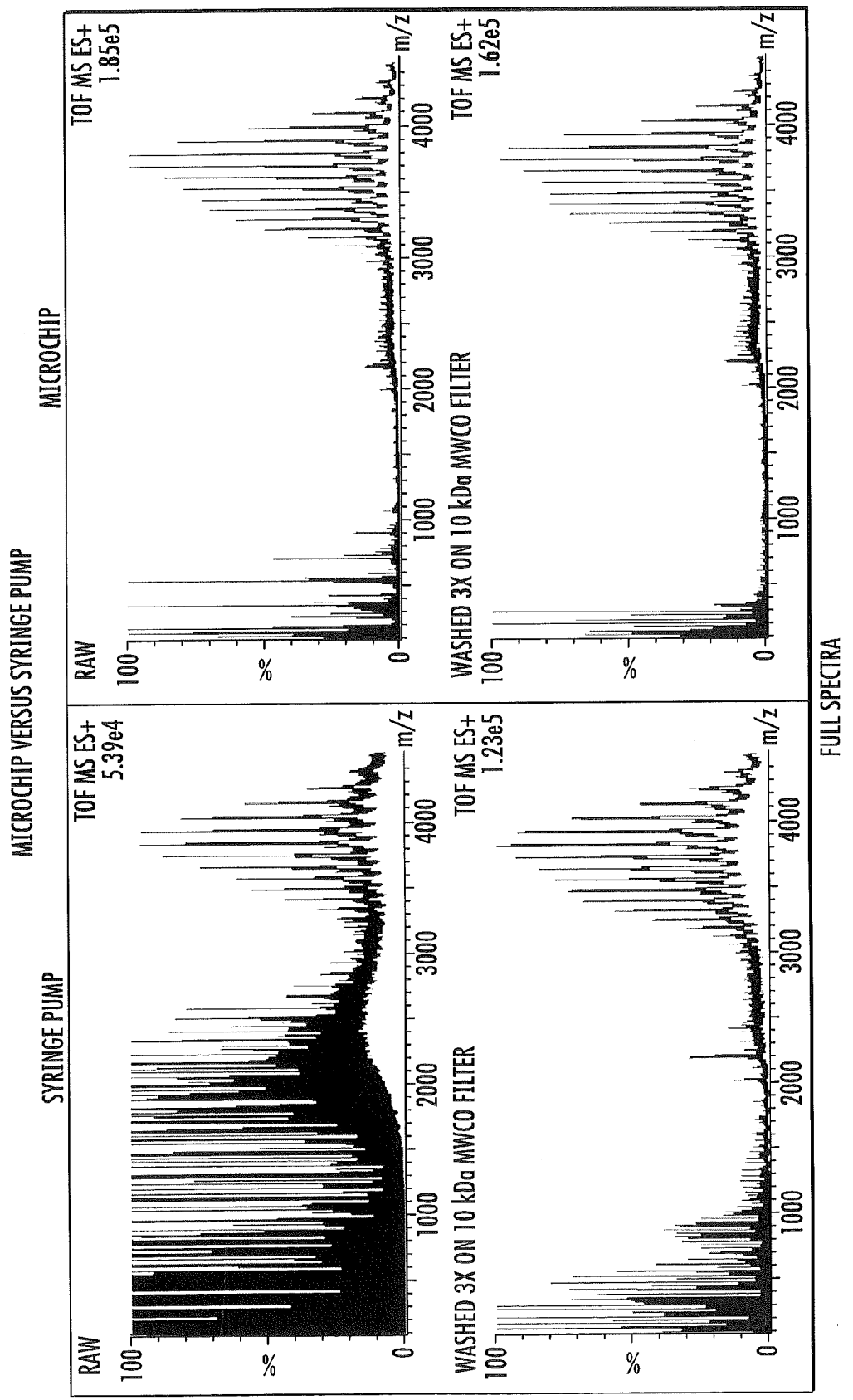
Figure 13:
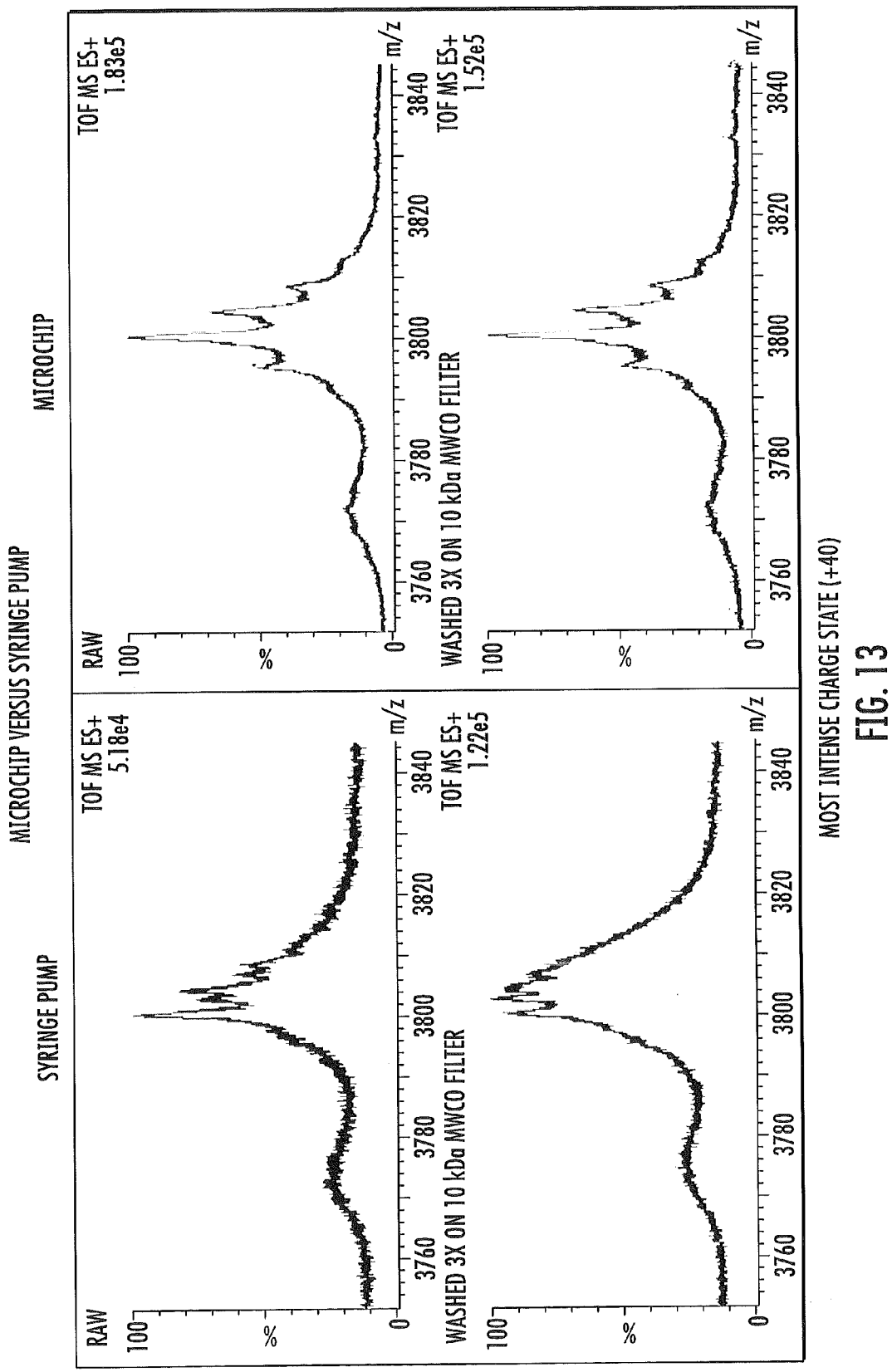
Figure 14:
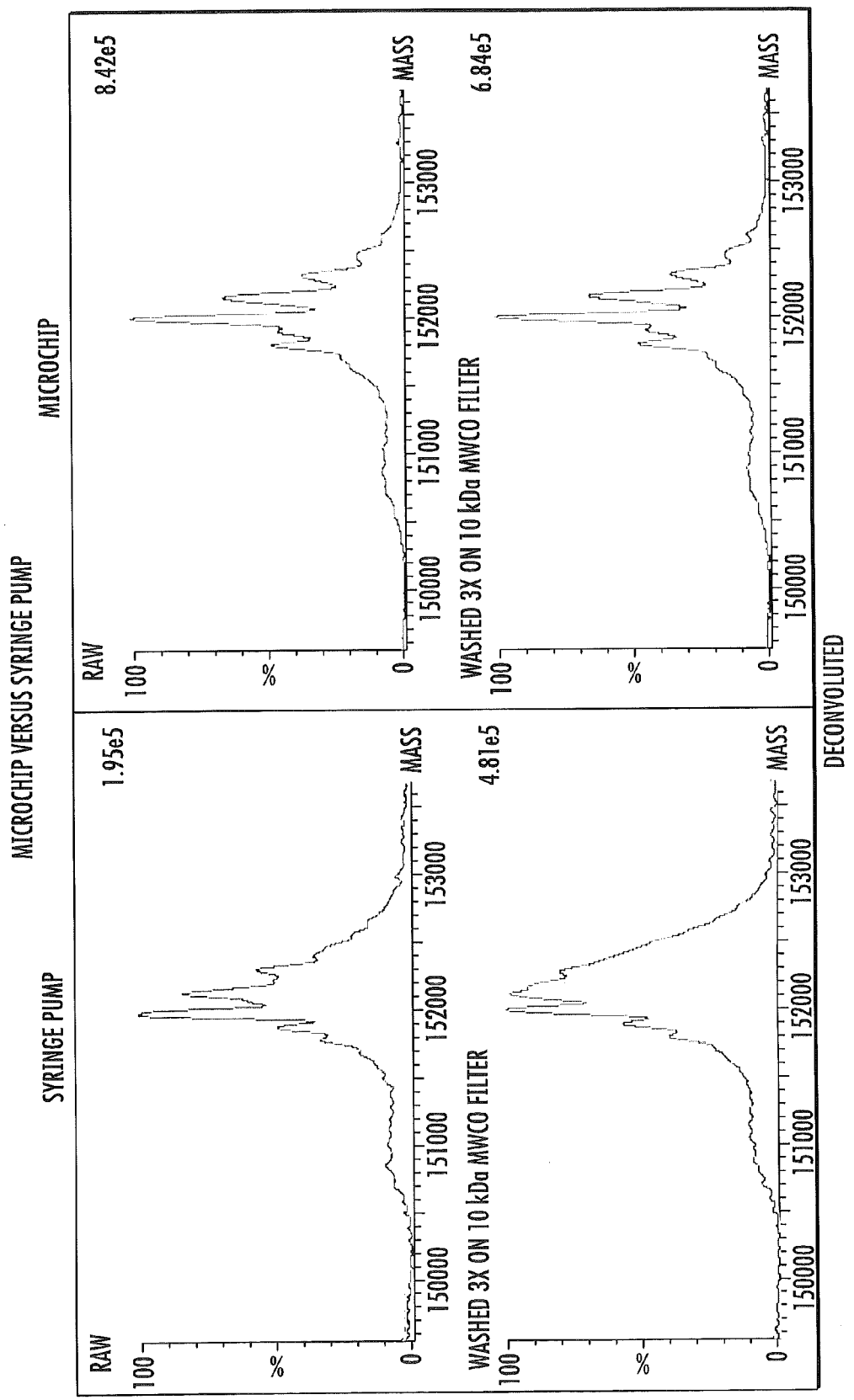
Figure 15:
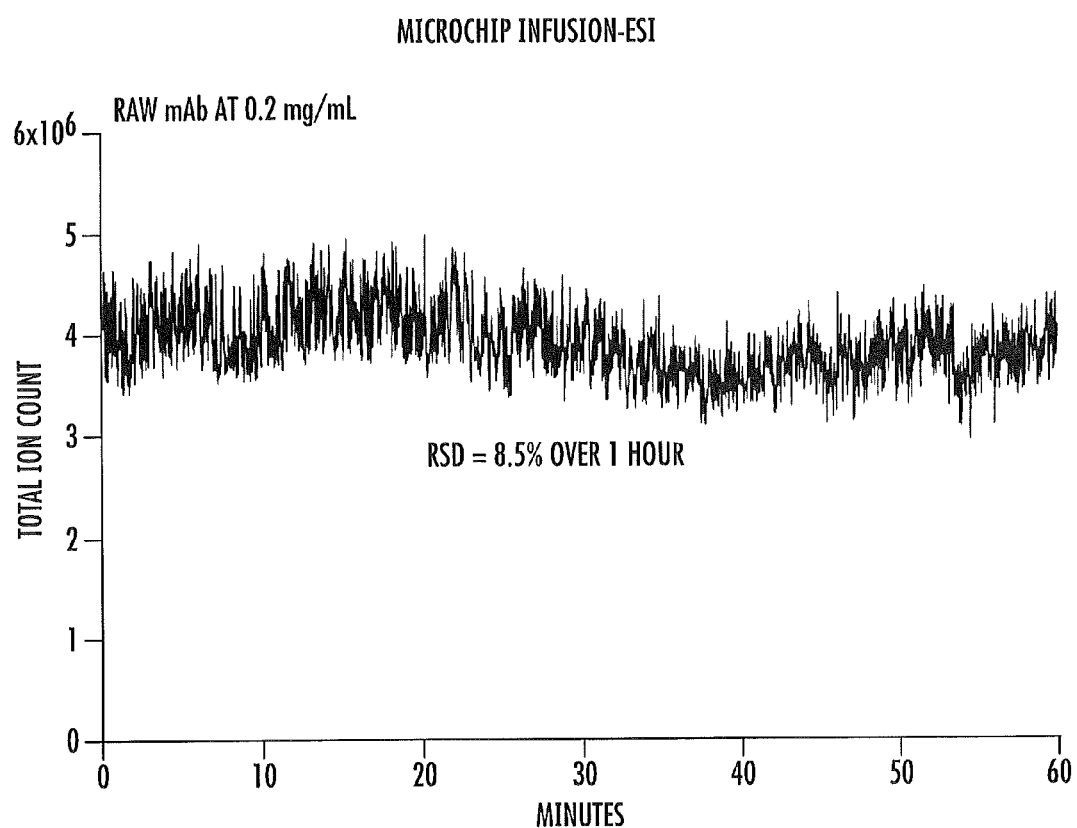
Figure 16:
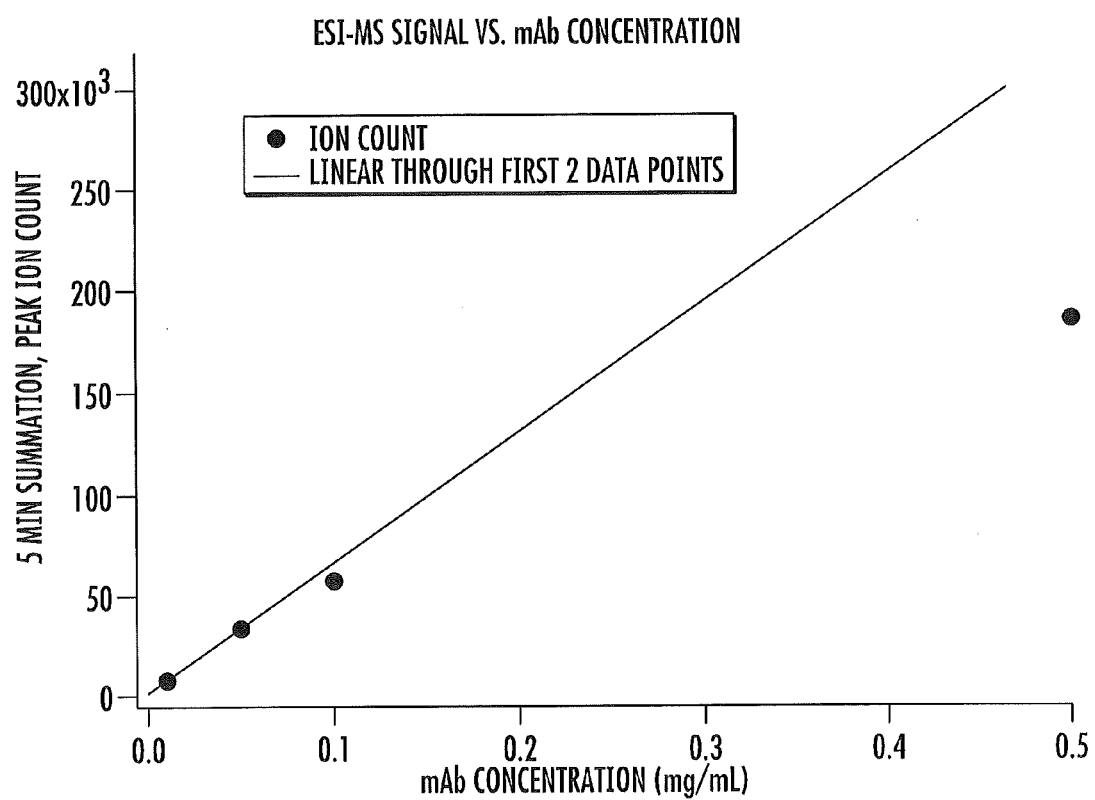

FIGS. 11-16 are graphs of mAB signal data. FIGS. 12-14 are graphs comparing syringe pump spectra to a microchip using differential axial transport for microchip infusion ESI.

The foregoing is illustrative of the present invention and is not to be construed as limiting thereof. Although a few exemplary embodiments of this invention have been That which is claimed:

1. A method of online sample processing for electrospray ionization (ESI), comprising:
providing a microfluidic device comprising:
a fluidic sample separation channel;
an ESI emitter in communication with the sample separation channel;
a sample reservoir in communication with the sample separation channel; and
a background electrolyte (BGE) channel connected to the sample separation channel at a junction proximate to the ESI emitter; and
selectively transporting at least one target analyte of the sample from the sample reservoir to the ESI emitter,
wherein selectively transporting the at least one target analyte comprises generating a first axial electroosmotic flow (EOF) along an axial direction in the sample separation channel in a direction away from the ESI emitter, and generating a second axial EOF in the BGE channel along an axial direction in the BGE channel in a direction toward the ESI emitter, the second axial EOF having a magnitude that is greater than a magnitude of the first axial EOF.

2. The method of claim 1, wherein the at least one target analyte comprises a protein, and wherein the sample further comprises at least one surfactant contaminant material, and wherein the selective transport is carried out so that the at least one surfactant contaminant material is not transported to the ESI emitter.

3. The method of claim 1, wherein the microfluidic device comprises a BGE reservoir connected to the BGE channel, wherein selectively transporting the at least one target analyte comprises applying a first voltage to the sample reservoir and applying a second voltage that is less than the first voltage to the BGE reservoir, wherein the transport of the at least one target analyte occurs in a direction against the first axial EOF and toward the ESI emitter.

4. The method of claim 3, wherein a magnitude of the second axial EOF is greater than a magnitude of the first axial EOF, and wherein the second axial EOF defines an EO pump that discharges fluid comprising the at least one target analyte from the ESI emitter.

5. The method of claim 1, wherein during the selective transport, high mobility cations of the at least one analyte migrate in a direction against the first axial EOF and toward the ESI emitter, and at least one of low mobility cations, anions, and neutral molecules of at least one contaminant material remain in the sample reservoir.

6. The method of claim 1, wherein during the selective transport, high mobility anions of the at least one analyte to migrate in a direction against the first axial EOF and toward the ESI emitter, and at least one of low mobility anions, cations, and neutral molecules of at least one contaminant material remain in the sample reservoir.

7. The method of claim 1, wherein the fluidic device is a capillary device with the separation channel defined by a capillary tube.

8. The method of claim 1, wherein the microfluidic device is a microchip.

9. The method of claim 1, wherein the at least one target analyte comprises intact monoclonal antibodies, and wherein the sample further comprises at least one surfactant contaminant material that is not transported to the ESI emitter.

10. The method of claim 1, further comprising:
discharging fluid comprising the at least one target analyte from the ESI emitter and into a mass spectrometer for at least 30 seconds; and
generating mass spectrometry information about the at least one target analyte using the mass spectrometer.

11. The method of claim 1, wherein the microfluidic device comprises a first surface coating disposed on interior surfaces of both the sample separation and BGE channels to impart a net positive or negative charge to the interior surfaces of the sample separation and BGE channels, and a second surface coating disposed only on the first surface coating within the separation channel to cause the magnitude of the first axial EOF to be different from the magnitude of the second axial EOF.

12. The method of claim 1, further comprising flowing a common BGE fluid in the sample separation and BGE channels before selectively transporting the at least one target analyte.

13. A mass spectrometer system, comprising:
a mass spectrometer with an inlet orifice;
a microfluidic device comprising a sample reservoir, a sample separation channel in fluid communication with the sample reservoir, a background electrolyte BGE) reservoir, a BGE channel in fluid communication with the BGE reservoir, and an electrospray ionization (ESI) emitter in fluid communication with the sample separation channel, wherein the BGE flow channel is connected to the sample separation channel at a junction proximate to the ESI emitter; and
a power source in electrical communication with the sample reservoir and the BGE reservoir,
wherein, in operation, the system generates electroosmotic flow (EOF) in the sample separation and BGE channels so that the EOF in the BGE channel has a greater magnitude and a different axial direction than the EOF in the sample separation channel to selectively transport at least one target analyte of a sample from the sample reservoir to the ESI emitter;
wherein the selectively transported at least one target analyte of the sample is emitted by the ESI emitter; and
wherein one or more non-analyte components of the sample are not transported from the sample reservoir to the ESI emitter; and
wherein the EOF in the sample separation channel is in an axial direction that is away from the ESI emitter, and the EOF in the BGE channel is in an axial direction that is toward the ESI emitter.

14. The system of claim 13, further comprising a control circuit configured to control application of an electric field by the power supply to the sample reservoir and to the BGE reservoir to selectively transport the at least one target analyte.

15. The system of claim 13, wherein an internal surface of the separation channel has a positive charge, and wherein, in operation, high mobility cations of the at least one target analyte migrate against the EOF in the sample separation channel and toward the ESI emitter, and at least one of low mobility cations, anions, and neutral molecules of the one or more non-analyte components remain in the sample reservoir.

16. The system of claim 13, wherein surfaces of the at least one separation channel have a negative charge, and wherein, in operation, the at least one separation channel is configured to allow high mobility anions of the analyte to migrate against the EOF in the separation channel toward the ESI emitter while low mobility anions, cations, and neutrals remain in the sample reservoir.

17. The system of claim 13, further comprising:
a first surface coating disposed on interior surfaces of both the sample separation channel and the BGE channel to impart a net positive or negative charge to the interior surfaces of the sample separation and BGE channels; and
a second surface coating disposed only on the first surface coating within the sample separation channel to cause the magnitude of the EOF in the sample separation channel to be different from the magnitude of the EOF in the BGE channel.

18. The system of claim 13, wherein, in operation, the system directs a common BGE fluid to flow in both the sample separation and BGE channels.

19. A microfluidic device for infusion-electro spray ionization-mass spectroscopy, comprising:
a background electrolyte (BGE) reservoir;
a BGE channel formed in at least one substrate material, the BGE channel being in fluid communication with the BGE reservoir;
a sample reservoir;
a separation channel formed in the at least one substrate material and having opposing ingress and egress ends, wherein:
the ingress end is in fluid communication with the sample reservoir;
the separation channel is connected to the BGE channel at a junction; and
an interior channel surface of the separation channel has a net positive or negative charge;
an electrospray ionization (ESI) emitter in fluid communication with the separation channel and the BGE channel and positioned downstream from the junction; and
a first coating material disposed on the interior channel surface of the separation channel but not on an interior channel surface of the BGE channel, wherein the first coating material reduces a magnitude of electroosmotic flow (EOF) in the separation channel, relative to EOF in the separation channel without the first coating material,
wherein, in operation, the magnitude of the EOF in the separation channel is at least 20% less than a magnitude of EOF in the BGE channel; and
wherein the EOF in the BGE channel defines an electroosmotic pump that discharges fluid from the separation channel through the ESI emitter; and
wherein, in operation, the EOF in the separation channel is in an axial direction that is away from the ESI emitter and the EOF in the BGE channel is in an axial direction that is toward the ESI emitter.

20. The device of claim 19, wherein the BGE reservoir, the BGE channel, the sample reservoir, the separation channel, and the ESI emitter are integrated on a microchip formed of the at least one substrate material.

21. The device of claim 19, further comprising:
a second coating material disposed in both the separation channel and the BGE channel to impart the net positive or negative charge to the interior channel surface of the separation channel,
wherein, in the separation channel, the second coating material is positioned between the at least one substrate material and the first coating material; and
wherein in the BGE channel, the second coating material is disposed on the interior channel surface of the BGE channel.

22. The device of claim 19, wherein, in operation, a common BGE fluid flows in both the separation and BGE channels.

* * * * *

UNITED STATES PATENT AND TRADEMARK OFFICE
CERTIFICATE OF CORRECTION

PATENT NO. : 9,502,225 B2  
APPLICATION NO. : 14/402278  
DATED : November 22, 2016  
INVENTOR(S) : Mellors et al.

Page 1 of 1

It is certified that error appears in the above-identified patent and that said Letters Patent is hereby corrected as shown below:

In the Claims

Column 17, Claim 6, Lines 58 and 59: Please correct "one analyte to migrate" to read -- one analyte migrate --

Column 18, Claim 13, Line 30: Please correct "BGE)" to read -- (BGE) --

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*